United States Patent [19]

Yoo et al.

[11] Patent Number: 5,236,935

[45] Date of Patent: Aug. 17, 1993

[54] BENZOPYRAN DERIVATIVES AND PROCESSES FOR THE PREPARATION THEREOF

[75] Inventors: Sung-Eun Yoo; Kyu Y. Yi; Nak C. Jeong; Jee H. Suh; Seon-Ju Kim; Hwa-Sup Shin; Byung H. Lee; Kyu S. Jung, all of Daejeon, Rep. of Korea

[73] Assignee: Korea Research Institute of Chemical Technology, Daejeon, Rep. of Korea

[21] Appl. No.: 886,986

[22] Filed: May 21, 1992

[51] Int. Cl.[5] .................. A61K 31/44; A61K 31/40; C07D 401/04; C07D 405/04
[52] U.S. Cl. .................. 514/337; 514/424; 514/456; 514/228.2; 514/233.5; 514/252; 514/256; 514/212; 514/414; 548/525; 548/464; 546/269; 544/58.2; 544/151; 544/377; 544/238; 544/310; 540/524
[58] Field of Search .............. 548/525, 464; 514/424, 514/337, 228.2, 233.5, 252, 256, 212, 414, 456; 546/269; 549/404; 544/58.2, 151, 377, 238, 310; 540/524

[56] References Cited

U.S. PATENT DOCUMENTS 4,997,846  5/1991  Genain et al. .................. 548/525

Primary Examiner—Mary Lee
Assistant Examiner—Joseph K. McKane
Attorney, Agent, or Firm—Thomas J. Dodd

[57] ABSTRACT

The present invention relates to novel benzopyran derivatives of formula (I) which have superior selectivity in the treatment of hypertension by lowering blood pressure with a relaxation activity on vascular smooth muscle. The present invention also relates to processes for preparing such compounds; and to a pharmaceutical compositions containing such compounds as an active ingredient.

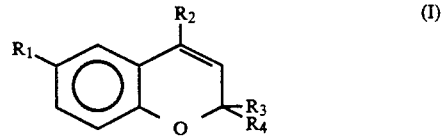

(I)

wherein:
$R_1$ is —CN, —NO$_2$, —OCX$_1$X$_2$X$_3$, —NH$_2$, —NHSO$_2$R$^A$,

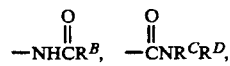

—SO$_2$R$^C$ or —SO$_2$NR$^C$R$^D$ wherein $X_1$, $X_2$ and $X_3$ are, each independently, a fluorine, chlorine or hydrogen atom; $R^A$ and $R^B$ are, each independently, an amino, C$_{1-6}$ alkoxy, C$_{1-6}$ alkyl group or an optionally substituted phenyl group; and $R^C$ and $R^D$ are a hydrogen atom, or a C$_{1-6}$ alkyl group or an optionally substituted phenyl group with a halogen atom, or a straight or branched C$_{1-3}$ alkyl group;

$R_2$ is

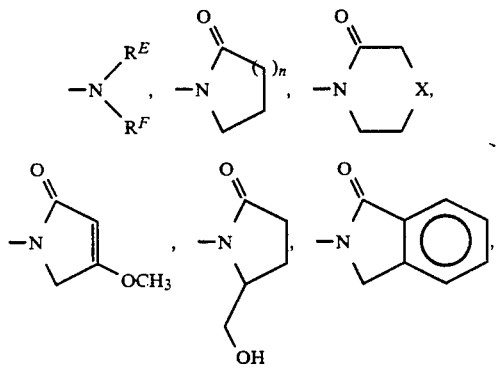

(Abstract continued on next page.)

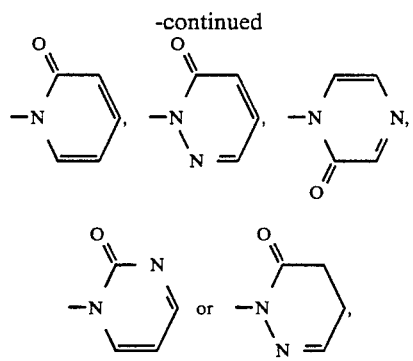

wherein $R^E$ is a hydrogen atom, or a $C_{1-6}$ alkyl, cyclopropyl, cyclopropylmethyl or benzyl group; $R^F$ is —$COR^A$ or —$CSR^A$; X is O, S or $NR^C$, and n is an integer from 0 to 3, wherein $R^A$ and $R^C$ have the same meanings as defined above;

$R_3$ is a $C_{1-4}$ straight or branched alkyl group; and $R_4$ is

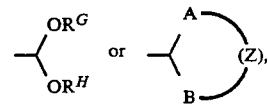

wherein $R^G$ and $R^H$ are, each independently, a $C_{-16}$ alkyl group or an optionally substituted phenyl group; A and B are, each independently, S or O; and Z is a $C_{1-3}$ straight or branched alkyl group.

5 Claims, No Drawings

BENZOPYRAN DERIVATIVES AND PROCESSES FOR THE PREPARATION THEREOF

FIELD OF THE INVENTION

The present invention relates to novel benzopyran derivatives which have a superior selectivity in the treatment of hypertension by lowering blood pressure with a relaxation activity on vascular smooth muscle. The present invention also relates to processes for preparing such compounds and to pharmaceutical compositions containing such compounds as an active ingredient.

BACKGROUND OF THE INVENTION

Hitherto, it has been known that a number of compounds which induce vascular smooth muscle to relax by inhibiting influx of calcium ions into cells are useful in the treatment of diseases in cardiac circulatory. As such compounds, for example, calcium channel inhibitors and sodium channel inhibitors have been already developed, and, further, many studies on potassium channel activators have been made. Examples of such potassium channel activators include Pinacidil used frequently as a capillary vasodilator drug; Nicorandil used as an anti-stenocardia drug; and Cromakalim used as an anti-hypertension agent.

European Patent Publication No. 093,535 filed by Beecham Group, plc. in the title of "novel chromene and chroman" discloses benzopyran derivatives of formula (A) and salts thereof:

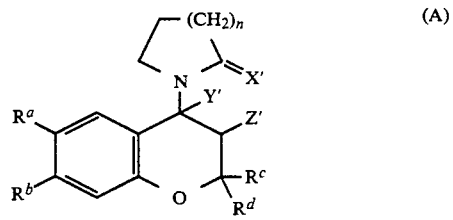

wherein:
one of $R^a$ and $R^b$ is a hydrogen atom and the other is selected from the group consisting of a $C_{1-6}$ alkyl- and alkoxycarbonyl, $C_{1-6}$ alkyl-carbonyloxy, $C_{1-6}$ alkylhydroxymethyl, nitro, cyano, chloro, trifluoromethyl, $C_{1-6}$ alkyl- and alkoxysulfinyl, $C_{1-6}$ alkyl- and alkoxysulfonyl, $C_{1-6}$ alkyl- and alkoxycarbonylamino, $C_{1-6}$ alkyl- and alkoxysulfinylamino, $C_{1-6}$ alkyl- and alkoxysulfonylamino, $C_{1-6}$ alkyl- and alkoxythicarbonyl, $C_{1-6}$ alkyl- and alkoxythiocarbonyloxy, $C_{1-6}$ alkylthiomethyl, formyl, an optionally substituted aminosulfinyl, aminosulfonyl or aminocarbonyl, or a terminal substituted ethylenyl, —C($C_{1-6}$ alkyl) NOH, and —C($C_{1-6}$ alkyl)NNH$_2$ group, or
one of $R^a$ and $R^b$ is nitro, cyano or a $C_{1-6}$ alkylcarbonyl group and the other is methoxy or an optionally substituted amino group;
one of $R^c$ and $R^d$ is a hydrogen atom or a $C_{1-4}$ alkyl group, and the other is a $C_{1-4}$ alkyl group, or
$R^c$ and $R^d$ together form a $C_{2-5}$ polymethylene;
X' is an oxygen or sulfur atom;
Y' and Z' are a hydrogen atom, respectively, or together form a single bond; and n is 1 or 2.

Further, European Patent Publication No. 298,452 A2 filed by F. Hoffmann La Roche & Co. discloses benzopyran derivatives of formula (B) and pharmaceutical compositions containing same:

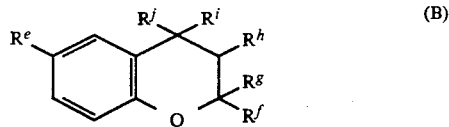

wherein:
$R^e$ is a hydrogen or halogen atom, or a trifluoromethyl, nitro, cyano, a lower alkyl, lower alkoxycarbonyl, lower alkylthio, lower alkylsulfonyl, lower alkanoyl, carbamoyl or mono- or di(lower alkyl) carbamoyl group;
$R^f$ is a hydrogen atom, or a lower alkyl or phenyl group;
$R^g$ is a hydrogen atom or a lower alkyl group;
$R^h$ is a hydrogen atom or a hydroxy group; and,
$R^i$ is a hydrogen atom; or $R^h$ and $R^i$ together form a single bond; and
$R^j$ is an aryl- or N-heteroaryl group whose 2-position is a hydroxy group, or an N-oxide group in the case of N-heteroaryl group.

The above compounds have been reported to be useful in the treatment of hypertension. However, another use of the compounds was reported in references such as Br. J. Pharmacol. 89, 395–405(1986), Br. J. Pharmacol. 165, 231–239(1989), and Br. J. Pharmacol. 95, 765–770(1988): i.e., the compounds may be used as a bronchodilator in addition to a blood pressure-lowering agent, since they can relax smooth muscle by enhancing the hyperpolarization of the plasma membrane of a cell. Accordingly, the above compounds have the disadvantage of a lower selectivity with respect to the anti-hypertension activity.

SUMMARY OF THE INVENTION

Accordingly, the present invention primarily pertains to novel benzopyran derivatives having superior selectivity in the treatment of hypertension. Further, the present invention relates to processes of preparing such compounds; and to pharmaceutical compositions containing such compounds as an active ingredient.

DETAILED DESCRIPTION OF THE INVENTION

The present invention provides novel benzopyran derivatives of formula (I)

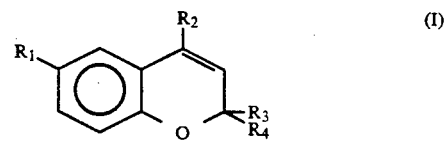

wherein:
$R_1$ is —CN, —NO$_2$, —OCX$_1$X$_2$X$_3$, —NH$_2$, —NHSO$_2$R$^A$,

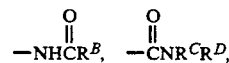

—SO$_2$R$^C$ or —SO$_2$NR$^C$R$^D$ wherein X$_1$, X$_2$ and X$_3$ are, each independently, a fluorine, chlorine or hydrogen atom; R$^A$ and R$^B$ are, each independently, an amino, $C_{1-6}$ alkoxy, $C_{1-6}$ alkyl group or an optionally substituted phenyl group; and $R^C$ and $R^D$ are, each independently, a hydrogen atom, or a $C_{1-6}$ alkyl group or an optionally substituted phenyl group with a halogen atom, or a straight or branched $C_{1-3}$ alkyl group;

$R_2$ is

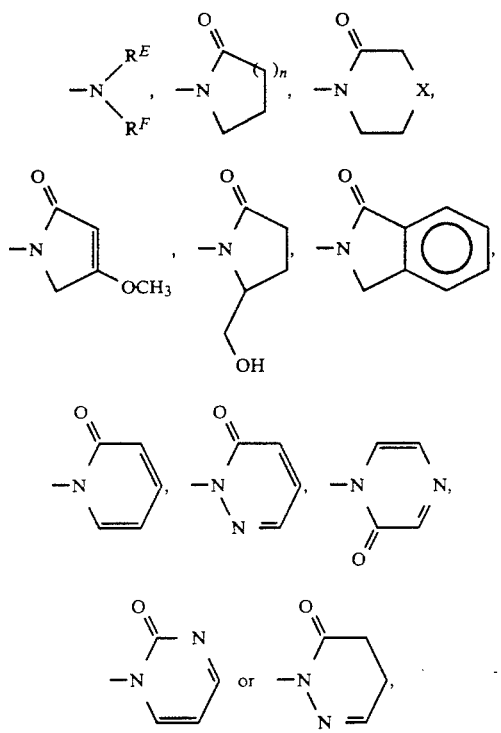

wherein $R^E$ is a hydrogen atom, or a $C_{1-6}$ alkyl, cyclopropyl, cyclopropylmethyl or benzyl group; $R^F$ is —$COR^A$ or —$CSR^A$; X is O, S or $NR^C$, and n is an integer from 0 to 3, wherein $R^A$ and $R^C$ have the same meanings as defined above;

$R_3$ is a $C_{1-4}$ straight or branched alkyl group; and $R_4$ is

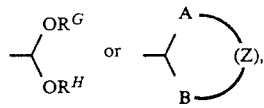

wherein $R^G$ and $R^H$ are, each independently, a $C_{1-6}$ alkyl group or an optionally substituted phenyl group; A and B are, each independently, S or O; and Z is a $C_{1-3}$ straight or branched alkyl group.

Preferred benzopyran derivatives of the present invention are the compounds of formula (I) wherein $R_1$ is —CN, —$NO_2$, —$OCF_3$ or —$SO_2NR^CR^D$ (wherein $R^C$ and $R^D$ are, each independently, a $C_{1-6}$ alkyl group), $R_2$ is

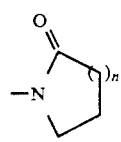

(wherein n is an integer from 0 to 2),

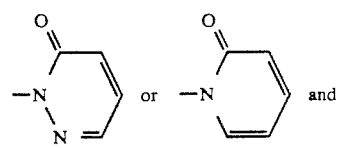

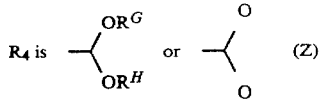

wherein $R^G$ and $R^H$ are, each independently, a $C_{1-3}$ alkyl group and Z is as defined above.

More preferred benzopyran derivatives of the present invention are the compounds of formula (I) wherein $R_1$ is —CN, —$NO_2$ or —$OCF_3$, $R_2$ is

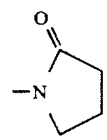

and $R_4$ is

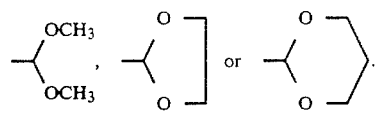

The novel benzopyran compounds of formula (I) may be present in the form of a racemic mixture of optically active isomers of formulae (I') and (I''). Each of the pure isomers may be obtained separately, which are also within the scope of the invention. Accordingly, the compounds of formula (I), include both isomers of formulae (I') and (I') as well as the racemic mixture thereof:

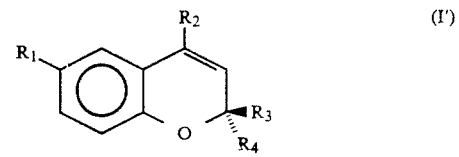

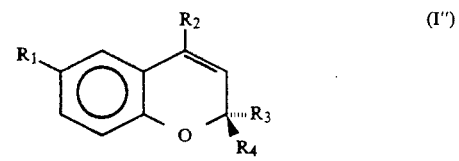

wherein $R_1$, $R_2$, $R_3$ and $R_4$ have the same meanings as defined above.

The present invention also provides novel processes for preparing the compounds of formula (I).

The benzopyran derivative having the formula (I) according to the present invention can be prepared by the following:

PROCESS 1

The compounds of the present invention can be prepared by using the following Reaction Scheme (1):

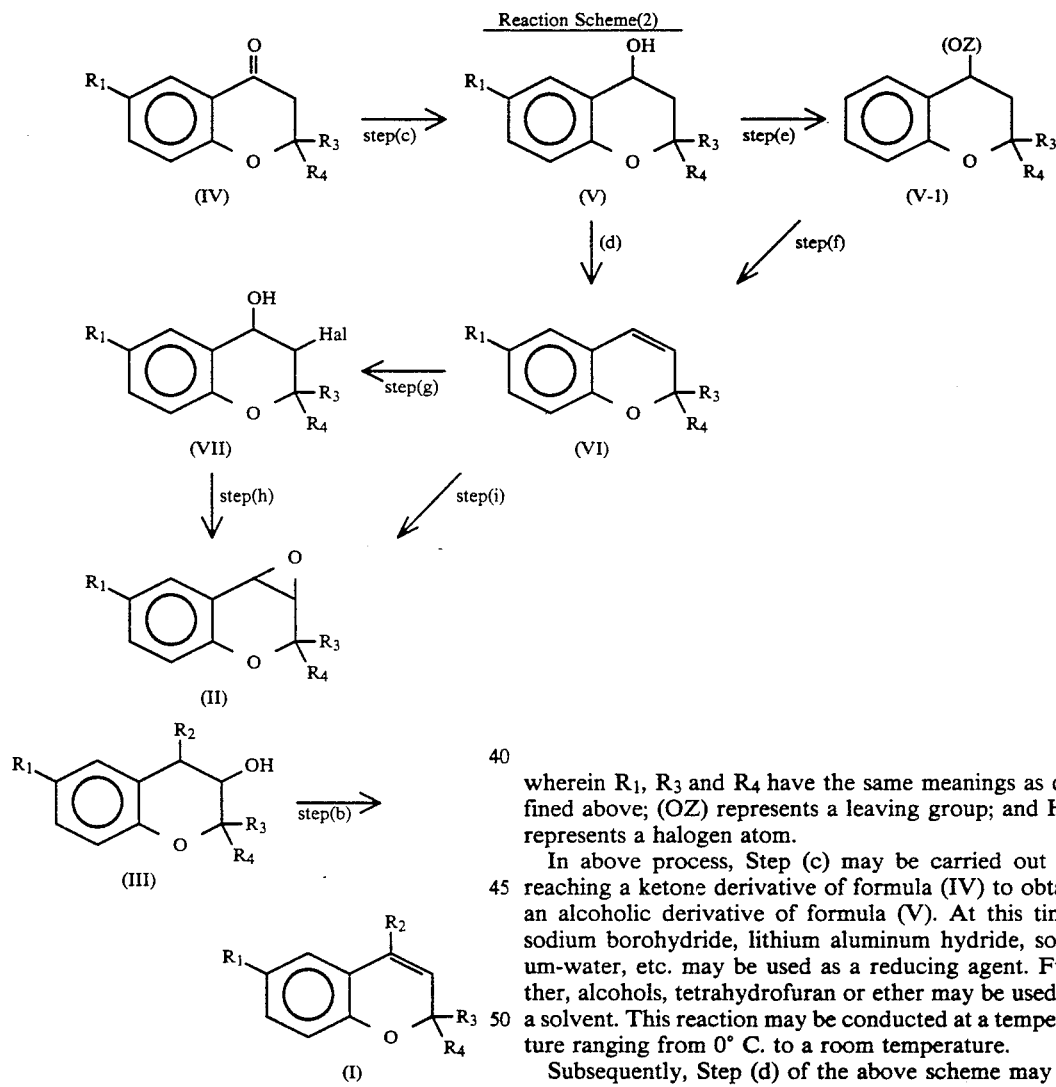

wherein $R_1$, $R_2$, $R_3$ and $R_4$ have the same meanings as defined above.

In the above process, Step (a) may be conducted by reacting an epoxy compound of formula (II) with a nucleophillic compound (containing a $R_2$ group) in the presence of a base and a solvent to provide an alcoholic derivative of formula (III). Examples of the base include sodium hydride, potassium t-butoxide, etc. Examples of a solvent that may be used in this step include dimethylformamide (DMF), tetrahydrofuran (THF), dimethylsulfoxide (DMSO) and alcohols. The reaction may be carried out at a room temperature.

Thereafter, Step (b) may be conducted by dehydrating the alcoholic compound of formula (III) in the presence of a base to provide the final compound of formula (I). The dehydration in Step (b) can be achieved at a room temperature or by heating the reactants to 60° C. in a solvent such as DMSO or DMF using sodium hydride as the base, or in a solvent such as water, dioxane or a mixture of water and dioxane using sodium hydroxide as the base.

An epoxy compound that may be employed as the starting material of the above process may be prepared by, for example, a process shown in the following Reaction Scheme (2):

wherein $R_1$, $R_3$ and $R_4$ have the same meanings as defined above; (OZ) represents a leaving group; and Hal represents a halogen atom.

In above process, Step (c) may be carried out by reaching a ketone derivative of formula (IV) to obtain an alcoholic derivative of formula (V). At this time, sodium borohydride, lithium aluminum hydride, sodium-water, etc. may be used as a reducing agent. Further, alcohols, tetrahydrofuran or ether may be used as a solvent. This reaction may be conducted at a temperature ranging from 0° C. to a room temperature.

Subsequently, Step (d) of the above scheme may be carried out by dehydrating the alcoholic derivative of formula (V) to provide a benzopyran derivative of formula (VI). A cuprous compound such as cuprous sulfate and cuprous chloride can be used as a catalyst in this step and the reaction temperature may be greater than 100° C.

Alternatively, the alcoholic derivative of formula (V) may be reacted with an appropriate mecyl chloride or tosyl chloride to give a mecylate or tosylate of formula (V-1) having a suitable leaving group (OZ) as shown in Step (e). Then, the leaving group (OZ) can be removed therefrom in the presence of a base to obtain the benzopyran derivative of formula (VI) as shown in Step (f).

The reaction of Step (e) may be conducted at a temperature ranging from 0° C. to a room temperature either in pyridine solvent or in a solvent such as dichloromethane and chloroform in the presence of a base, e.g., a tertiary amine; and, a catalyst such as 4-dimethylaminopyridine (DMAP) may be used in a catalytic amount.

In Step (f), a base such as 1,8-diazabicyclo[5,4,0]unde-7-cene (DBU), potassium t-butoxide or sodium ethoxide may be used; and, as the corresponding solvent to the above bases, benzene, toluene, t-butanol or ethanol can be used. The reaction temperature may range from a room temperature to the boiling point of the solvent.

Step (g) of the scheme may be conducted by halohydrinating the benzopyran derivative of formula (VI) to a halohydrin derivative of formula (VII). Examples of halogen atom-donating agent used for the halohydrination include N-bromosuccinamide, N-chloro-succinamide and bromine. The reaction is carried out in a solvent such as water and water-dimethylsulfoxide at a temperature ranging from 0° C. to a room temperature.

Step (h) of the process may be conducted by reacting the halohydrin derivative of formula (VII) with a base to provide an epoxy compound of formula (II). Examples of the base include sodium hydroxide, sodium hydride, potassium hydride, potassium t-butoxide, etc. The reaction may be carried out in a solvent such as dioxane and dioxane-water mixture at a temperature ranging from 0° C. to a room temperature. If necessary, sodium iodide may be used as a catalyst in a catalytic amount.

Alternatively, the benzopyran derivative of formula (VI) obtained in step (f) may be directly oxidized to the epoxy derivative of formula (II) using an oxidizing agent, as shown in step (i). In this step, m-chloroperbenzoic acid, hydrogen peroxide or magnesium monoperoxyphthalate may be used as the oxidizing agent; and dichloromethane or chloroform may be used as a solvent; or, dimethyloxiran may be used as the oxidizing agent and dichloromethane or acetone-dichloromethane may be used as a solvent. If necessary, oxon and acetone may be mixed in an aqueous sodium hydrogen carbonate solution to produce dimethyloxiran in situ at a reaction temperature ranging from 0° C. to a room temperature.

In step (g) of the above scheme, a mixture of diastereomers of formulae (VII') and (VII'') is commonly obtained at a ratio of 1:1

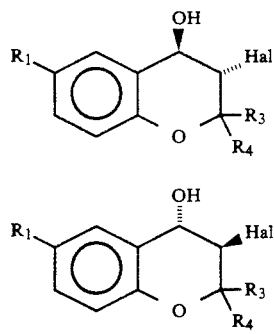

Accordingly, the epoxy compound of formula (II), the end product of the above scheme, is also commonly obtained as a mixture of the compounds of formulae (II') and (II''), which can be separated by employing a conventional method such as chromatography.

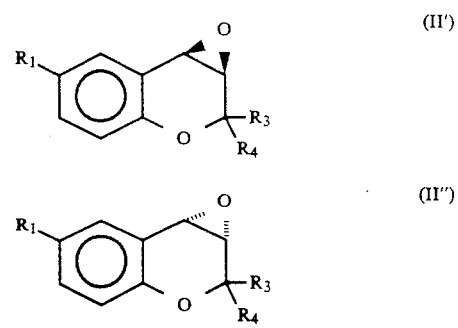

Since the stereoisomerism of the compounds of formulae (II') and (II'') is disappeared in the compound of formula (I), the reaction after Step (h) may be conducted using any of the compounds of formula (II') and (II''), and a mixture thereof.

The starting epoxy compounds of formula (II) may be also prepared from a propagyl ether derivative [see J. Med. Chem. 26, 1582 (1983)].

PROCESS 2

Among the compounds represented by the formula (I), more preferred compounds of formula (I-a) and (I-b) can be prepared by a process shown in the following Reaction Scheme (3):

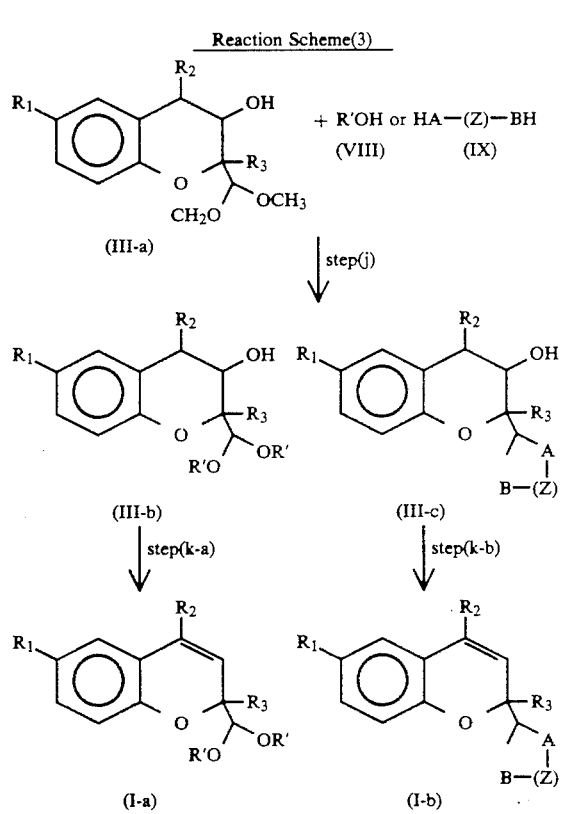

wherein $R_1$, $R_2$, $R_3$, A, B and Z have the same meanings as defined above; and R' is a $C_{2-6}$ alkyl group or an optionally substituted phenyl group.

In the above process, Step (j) can be conducted by transacetallization of a compound of formula (III-a) with an excess amount of an alcohol of formula (VIII), or a diol or mercaptoalcohol of formula (IX) to provide a compound of formula (III-b) or (III-c), respectively. An acid catalyst can be usd in a catalytic amount; and examples of the acid catalyst include a conventional Lewis acid such as boron trifluoride and p-toluene sulfonic acid. When a Lewis acid is employed as the catalyst, a halogen substituted solvent such as dichloromethane and chloroform can be used; and when p-toluene sulfonic acid is employed as the catalyst, a solvent such as benzene and toluene can be used. The reaction temperature may range from a room temperature to the boiling point of the solvent employed.

Step (k-a) or (k-b) is then conducted by dehydrating the compound of formula (III-b) or (III-c) in the presence of a base to obtain the preferred compound of formula (I-a) or (I-b), respectively. In this step, when sodium hydride is employed as the base, a solvent such as DMSO and DMF may be used together, or when sodium hydroxide is employed as the base, a solvent such as water, dioxane and water-dioxane may be used together. The reaction temperature may range from a room temperature to 60° C.

Among the above processes, Prcess 2 is more useful since the compounds containing —OCH$_3$ group in R$_3$ position are commercially available; and the desired compounds can be easily prepared therefrom by employing the transacetallization method.

The present invention also provides a process for preparing each of the compounds of formulae (I') and (I''), separately.

Each of the optically active compounds of formulae (I') and (I'') may be obtained effectively, for example, by a process shown in the following Reaction Scheme (4):

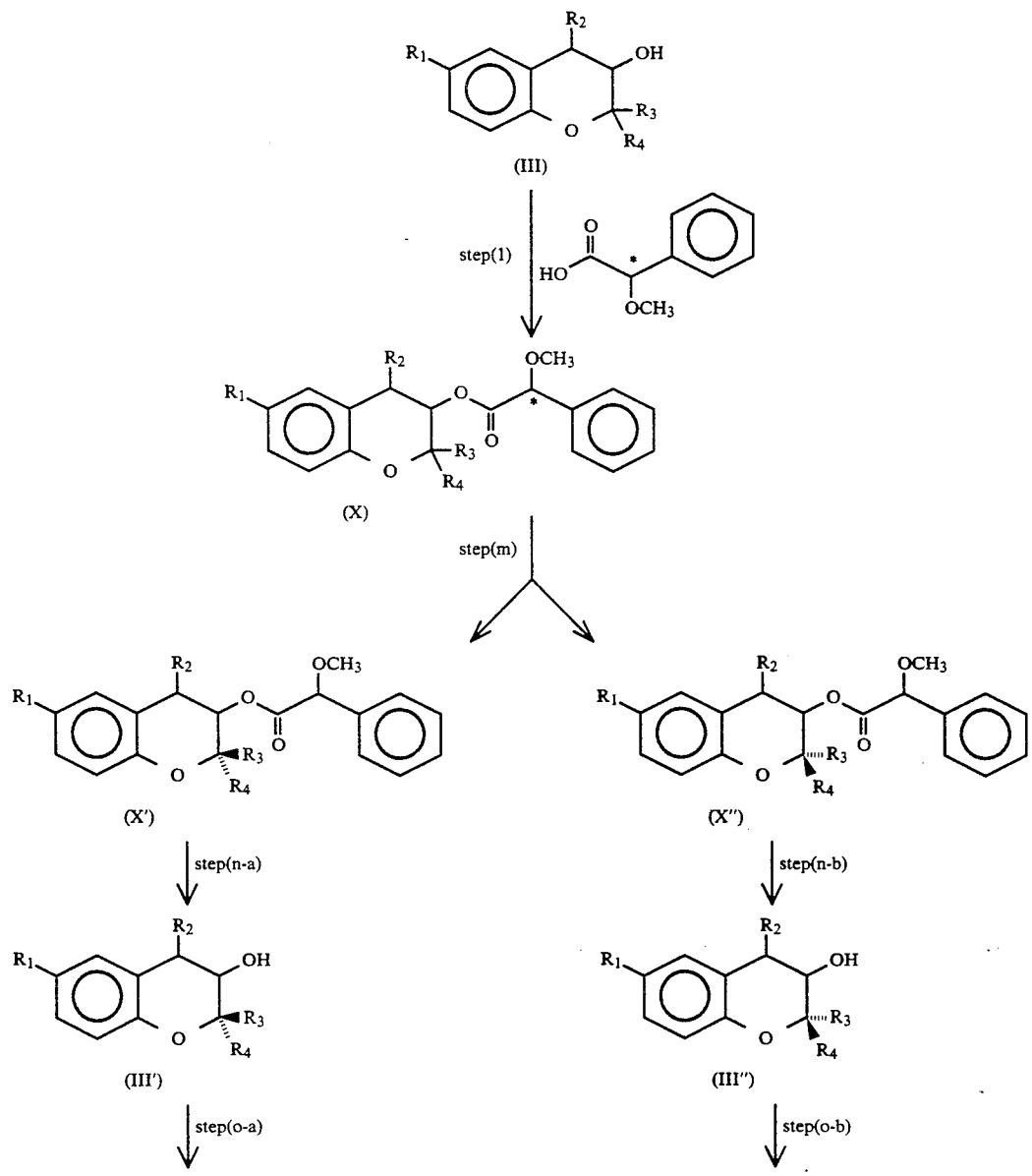

-continued
Reaction Scheme(4)

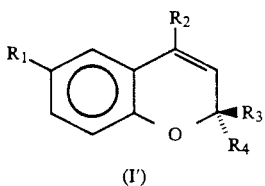

(I')

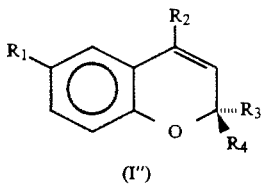

(I'')

wherein $R_1$, $R_2$, $R_3$ and $R_4$ have the same meanings as defined above.

In above process, Step (l) may be conducted by reacting an alcoholic derivative of formula (III) with an organic acid containing a chiral carbon such as (−)-α-methoxyphenylacetic acid in the presence of a condensation promoting agent and a catalyst to give an ester derivative of formula (X). Examples of the condensation promoting agent include N,N-disubstituted carbodiimides such as N,N-dicyclohexylcarboimide, and imidazols such as N,N-carbonyldiimidazole. Examples of the useful catalyst include 4-dimethylaminopyridin, etc. Further, a solvent such as ethyl acetate and dichloromethane may be used.

Step (m) may be conducted by resolving diastereomeric mixtures of formula (X) into each of diasteromers of formula (X') and (X'') by employing a conventional silica gel column chromatography or a crystallization method.

Step (n-a) or (n-b) may be conducted by hydrolyzing each of the resolved diastereomers to obtain the compounds of formulae (III') and (III'') which are optically active, respectively. A base such as sodium hydroxide, potassium hydroxide and lithium hydroxide, etc. and a solvent such as alcohols (for example, methanol, etc.), alcohol-water mixture, THF-water, dioxane-water, etc. may be used in the hydrolysis procedure.

Finally, Step (o-a) or (o-b) may be conducted by dehydrating each of the alcoholic derivative isomers of formulae (III') and (III'') in the presence of a base to obtain each of the optical isomers of formulae (I') and (I''). The reaction conditions of this step are the same as those of step (b) in Reaction Scheme (1).

Preferred compounds of formula (I) of the present invention prepared by the above-mentioned processes are as follows:

2-(2''-(1'',3''-dioxolane))-2-methyl-4-(2'-oxo-1'-pyrrolidinyl)-6-nitro-2H-1-benzopyran;
2-(2''-(1'',3''-dioxolane))-2-methyl-4-(2'-oxo-1'-pyrrolidinyl)-6-cyano-2H-1-benzopyran;
2-(2''-(1'',3''-dioxolane))-2-methyl-4-(2'-oxo-1'-pyrrolidinyl)-6-trifluoromethoxy-2H-1-benzopyran;
2-(2''-(1'',3''-dioxolane))-2-methyl-4-(2'-oxo-1'-pyrrolidinyl)-6-phenylsulfonylamido-2H-1-benzopyran;
2-(2''-(1'',3''-dioxolane))-2-methyl-4-(2'-oxo-1'-pyrrolidinyl)-6-phenylsulfonyl-2H-1-benzopyran;
2-(2''-(1'',3''-dioxane))-2-methyl-4-(2'-oxo-1'-pyrrolidinyl)-6-nitro-2H-1-benzopyran;
2-(2''-(1'',3''-dioxane))-2-methyl-4-(2'-oxo-1'-pyrrolidinyl)-6-cyano-2H-1-benzopyran;
2-(2''-(1'',3''-dioxane))-2-methyl-4-(2'-oxo-1'-pyrrolidinyl)-6-trifluoromethoxy-2H-1-benzopyran;
2-(2''-(1'',3''-dioxane))-2-methyl-4-(2'-oxo-1'-pyrrolidinyl)-6-phenylsulfonylamido-1H-1-benzopyran;
2-(2''-(1'',3''-dioxane))-2-methyl-4-(2'-oxo-1'-pyrrolidinyl)-6-phenylsulfonyl-2H-1-benzopyran;
2-dimethoxymethyl-2-methyl-4-(2'-oxo-1'-pyrrolidinyl)-6-nitro-2H-1-benzopyran;
2-dimethoxymethyl-2-methyl-4-(2'-oxo-1'-pyrrolidinyl)-6-cyano-2H-1-benzopyran;
2-dimethoxymethyl-2-methyl-4-(2'-oxo-1'-pyrrolidinyl)-6-trifluoromethoxy-2H-1-benzopyran;
2-dimethoxymethyl-2-methyl-4-(2'-oxo-1'-pyrrolidinyl)-6-phenylsulfonylamido-2H-1-benzopyran;
2-dimethoxymethyl-2-methyl-4-(2'-oxo-1'-pyrrolidinyl)-6-phenylsulfonyl-2H-1-benzopyran;
2-diethoxymethyl-2-methyl-4-(2'-oxo-1'-pyrrolidinyl)-6-nitro-2H-1-benzopyran;
2-diethoxymethyl-2-methyl-4-(2'-oxo-1'-pyrrolidinyl)-6-cyano-2H-1-benzopyran;
2-diethoxymethyl-2-methyl-4-(2'-oxo-1'-pyrrolidinyl)-6-trifluoromethoxy-2H-1-benzopyran;
2-diethoxymethyl-2-methyl-4-(2'-oxo-1'-pyrrolidinyl)-6-phenylsulfonylamido-2H-1-benzopyran;
2-diethoxymethyl-2-methyl-4-(2'-oxo-1'-pyrrolidinyl)-6-phenylsulfonyl-2H-1-benzopyran;
2-(2''-(1'',3''-dioxolane))-2-methyl-4-(1'-(2'-oxo-1',2'-dihydropyridazinyl))-6-nitro-2H-1-benzopyran;
2-(2''-(1'',3''-dioxolane))-2-methyl-4-(1'-(2'-oxo-1',2'-dihydropyridazinyl))-6-cyano-2H-1-benzopyran;
2-(2''-(1'',3''-dioxolane))-2-methyl-4-(1'-(2'-oxo-1',2'-dihydropyridazinyl))-6-trifluoromethoxy-2H-1-benzopyran;
2-(2''-(1'',3''-dioxolane))-2-methyl-4-(1'-(2'-oxo-1',2'-dihydropyridazinyl))-6-phenylsulfonylamido-2H-1-benzopyran;
2-(2''-(1'',3''-dioxolane))-2-methyl-4-(1'-(2'-oxo-1',2'-dihydropyridazinyl))-6-phenylsulfonyl-2H-1-benzopyran;
2-(2''-(1'',3''-dioxane))-2-methyl-4-(1'-(2'-oxo-1',2'-dihydropyridazinyl))-6-nitro-2H-1-benzopyran;
2-(2''-(1'',3''-dioxane))-2-methyl-4-(1'-(2'-oxo-1',2'-dihydropyridazinyl))-6-cyano-2H-1-benzopyran;
2-(2''-(1'',3''-dioxane))-2-methyl-4-(1'-(2'-oxo-1',2'-dihydropyridazinyl))-6-trifluoromethoxy-2H-1-benzopyran;
2-(2''-(1'',3''-dioxane))-2-methyl-4-(1'-(2'-oxo-1',2'-dihydropyridazinyl))-6-phenylsulfonylamido-2H-1-benzopyran;
2-(2''-(1'',3''-dioxane))-2-methyl-4-(1'-(2'-oxo-1',2'-dihydropyridazinyl))-6-phenylsulfonyl-2H-1-benzopyran;
2-dimethoxymethyl-2-methyl-4-(1'-(2'-oxo-1',2'-dihydropyridazinyl))-6-nitro-2H-1-benzopyran;
2-dimethoxymethyl-2-methyl-4-(1'-(2'-oxo-1',2'-dihydropyridazinyl))-6-cyano-2H-1-benzopyran;
2-dimethoxymethyl-2-methyl-4-(1'-(2'-oxo-1',2'-dihydropyridazinyl))-6-trifluoromethoxy-2H-1-benzopyran;
2-dimethoxymethyl-2-methyl-4-(1'-(2'-oxo-1',2'-dihydropyridazinyl))-6-phenylsulfonylamido-2H-1-benzopyran;
2-dimethoxymethyl-2-methyl-4-(1'-(2'-oxo-1',2'-dihydropyridazinyl))-6-phenylsulfonyl-2H-1-benzopyran;

2-diethoxymethyl-2-methyl-4-(1'-(2'-oxo-1',2'-dihydropyridazinyl))-6-nitro-2H-1-benzopyran;

2-diethoxymethyl-2-methyl-4-(1'-(2'-oxo-1',2'-dihydropyridazinyl))-6-cyano-2H-1-benzopyran;

2-diethoxymethyl-2-methyl-4-(1'-(2'-oxo-1',2'-dihydropyridazinyl))-6-trifluoromethoxy-2H-1-benzopyran;

2-diethoxymethyl-2-methyl-4-(1'-(2'-oxo-1',2'-dihydropyridazinyl))-6-phenylsulfonylamido-2H-1-benzopyran;

2-diethoxymethyl-2-methyl-4-(1'-(2'-oxo-1',2'-dihydropyridazinyl))-6-phenylsulfonyl-2H-1-benzopyran;

2-(2''-(1'',3''-dioxolane))-2-methyl-4-(1'-(2'-oxo-1',2'-dihydropyridyl))-6-nitro-2H-1-benzopyran;

2-(2''-(1'',3''-dioxolane))-2-methyl-4-(1'-(2'-oxo-1',2'-dihydropyridyl))-6-cyano-2H-1-benzopyran;

2-(2''-(1'',3''-dioxolane))-2-methyl-4-(1'-(2'-oxo-1',2'-dihydropyridyl))-6-trifluoromethoxy-2H-1-benzopyran;

2-(2''-(1'',3''-dioxolane))-2-methyl-4-(1'-(2'-oxo-1',2'-dihydropyridyl))-6-phenylsulfonylamido-2H-1-benzopyran;

2-(2''-(1'',3''-dioxolane))-2-methyl-4-(1'-(2'-oxo-1',2'-dihydropyridyl))-6-phenylsulfonyl-2H-1-benzopyran;

2-(2''-(1'',3''-dioxane))-2-methyl-4-(1'-(2'-oxo-1',2'-dihydropyridyl))-6-nitro-2H-1-benzopyran;

2-(2''-(1'',3''-dioxane))-2-methyl-4-(1'-(2'-oxo-1',2'-dihydropyridyl))-6-cyano-2H-1-benzopyran;

2-(2''-(1'',3''-dioxane))-2-methyl-4-(1'-(2'-oxo-1',2'-dihydropyridyl))-6-trifluoromethoxy-2H-1-benzopyran;

2-(2''-(1'',3''-dioxane))-2-methyl-4-(1'-(2'-oxo-1',2'-dihydropyridyl))-6-phenylsulfonylamido-2H-1-benzopyran;

2-(2''-(1'',3''-dioxane))-2-methyl-4-(1'-(2'-oxo-1',2'-dihydropyridyl))-6-phenylsulfonyl-2H-1-benzopyran;

2-dimethoxymethyl-2-methyl-4-(1'-(2'-oxo-1',2'-dihydropyridyl))-6-nitro-2H-1-benzopyran;

2-dimethoxymethyl-2-methyl-4-(1'-(2'-oxo-1',2'-dihydropyridyl))-6-cyano-2H-1-benzopyran;

2-dimethoxymethyl-2-methyl-4-(1'-(2'-oxo-1',2'-dihydropyridyl))-6-trifluoromethoxy-2H-1-benzopyran;

2-dimethoxymethyl-2-methyl-4-(1'-(2'-oxo-1',2'-dihydropyridyl))-6-phenylsulfonylamido-2H-1-benzopyran;

2-dimethoxymethyl-2-methyl-4-(1'-(2'-oxo-1',2'-dihydropyridyl))-6-phenylsulfonyl-2H-1-benzopyran;

2-diethoxymethyl-2-methyl-4-(1'-(2'-oxo-1',2'-dihydropyridyl))-6-nitro-2H-1-benzopyran;

2-diethoxymethyl-2-methyl-4-(1'-(2'-oxo-1',2'-dihydropyridyl))-6-cyano-2H-1-benzopyran;

2-diethoxymethyl-2-methyl-4-(1'-(2'-oxo-1',2'-dihydropyridyl))-6-trifluoromethoxy-2H-1-benzopyran;

2-diethoxymethyl-2-methyl-4-(1'-(2'-oxo-1',2'-dihydropyridyl))-6-phenylsulfonylamido-2H-1-benzopyran; and 2-diethoxymethyl-2-methyl-4-(1'-(2'-oxo-1',2'-dihydropyridyl))-6-phenylsulfonyl-2H-1-benzopyran.

As mentioned above, the compounds of formula (I) of the present invention have superior selectivity in the treatment of hypertension by lowering blood pressure with a relaxation activity on vascular smooth muscle.

The present invention also provides pharmaceutical compositions containing the compounds of formula (I) of the present invention as an active ingredient. Particularly, the present invention provides a pharmaceutical composition containing an effective amount of the compound of formula (I) and a conventional and pharmeceutically acceptable carrier.

The composition of the present invention can be formulated for oral or other forms of administration, preferably oral administration. The formulated compositions are preferably in the form of a unit dose. Examples of suitable unit-dose forms are tablet, capsule and powder. The effective unit dose may comprise 0.01 to 50 mg, preferably 0.01 to 10 mg of the compound of the present invention.

The composition of the present invention may be formulated with conventional additives, for example, a filler, dispersant, binder, lubricant, favoring agent, etc. The formulation of the composition can be conducted by using a known method in the art.

The following Preparation Examples and Examples are intended to illustrate how some of the compounds of the present invention can be prepared, without limiting its scope.

PREPARATION EXAMPLE

Synthesis of 2-dimethoxymethyl-2-methyl-3,4-epoxy-6-cyano-3,4-dihydro-2H-1-benzopyran Step 1) Synthesis of 2-dimethoxymethyl-2-methyl-4-oxo-6-cyano-3,4-dihydro-2H-1-benzopyran In 100 ml of toluene were dissolved 8.06 g (50 mmole) of 3-acetyl-4-hydroxybenzonitrile and 7.68 g (65 mmole) of pyruvic aldehyde dimethyl acetal; and, then 1.67 ml (20 mmole) of pyrrolidine was added thereto at room temperature. 30 minutes thereafter, the reactants were heated to reflux for 8 hours using Dean-Stark apparatus; the solvent was removed under reduced pressure; and, 50 ml of 2N HCl solution was added thereto. The resultant solution was stirred for 30 minutes at room temperature, extracted with ethyl acetate (100 ml×2), washed with 50 ml of water and with 50 ml of saturated sodium chloride aqueous solution, and purified by silica gel column chromatography using a mixture of hexane and ethyl acetate (4:1) as an eluent to obtain 11.19 g (yield 86%) of the title compound in the form of a white solid.

Step 2) Synthesis of 2-dimethoxymethyl-2-methyl-4-hydroxy-6-cyano-3,4-dihydro-2H-1-benzopyran In 200 ml of methanol was dissolved 11.19 g (43 mmole) of the compound obtained in step 1 and 1.62 g (43 mmole) of sodium borohydride was slowly added thereto. After the reaction mixture was stirred at 0° C. for 1 hour, methanol was removed therefrom under reduced pressure; and 100 ml of water was added to the residue so obtained. The resultant solution was extracted with ethyl acetate (200 ml×2), washed with 50 ml of saturated sodium chloride aqueous solution, dried over anhydrous magnesium sulfate, and evaporated under reduced pressure to obtain 11 g (yield 97%) of the title compound.

Step 3) Synthesis of 2-dimethoxymethyl-2-methyl-6-cyano-2H-1-benzopyran

In 100 ml of chloroform was dissolved 10.0 g (38 mmole) of the compound obtained in step 2; and, 13 ml (76 mmole) of N,N-diisopropylethylamine and 5.9 ml (76 mmole) of methanesulfonyl chloride were added thereto. The resultant solution was stirred for 15 hours at room temperature, diluted with 200 ml of chloroform and washed with 200 ml of water and with 200 ml of saturated sodium chloride solution. The organic layer was dried over anhydrous magnesium sulfate, filtered and evaporated to obtain a mixture of the desired compound and a chloride. The mixture was dissolved in 50 ml of toluene again; and 11 ml (76 mmole) of DBU (1,8-diazabicyclo[5,4,0]unde-7-cene) was added thereto. The resultant solution was heated to reflux for 6 hours and evaporated under reduced pressure to remove toluene solvent. The residue so obtained was extracted with ethyl acetate (200 ml×2), washed with 100 ml of water and with 50 ml of a saturated sodium chloride solution, dried over anhydrous magnesium sulfate, filtered and concentrated under reduced pressure to obtain residues, which were purified by silica gel column chromatography using a mixture of hexane and ethyl acetate (4:1) as an eluent to obtain 7.2 g (yield 77%) of the title compound.

Step 4) Synthesis of 2-dimethoxymethyl-2-methyl-3-bromo-4-hydroxy-6-cyano-3,4-dihydro-2H-1-benzopyran In 400 ml of DMSO was dissolved 7.2 g (29.4 mmole) of the compound obtained in step 3; and, 1.3 ml (73.3 mmole) of water and 11.1 g (62.3 mmole) of N-bromosuccinamide were added at 0° C. thereto. The resultant solution was stirred at 0° C. for 30 minutes, diluted with 200 ml of water, washed with ethyl acetate (200 ml×2), dried over anhydrous magnesium sulfate, filtered and concentrated to obtain residues, which were purified by silica gel column chromatography using a mixture of hexane and ethyl acetate (3:1) as an eluent to obtain 4.02 g (yield 40%) and 3.82 g (yield 38%) of each of diastereomers the title compound.

Step 5) Synthesis of 2-dimethoxymethyl-2-methyl-3,4-epoxy-6-cyano-3,4-dihydro-2H-1-benzopyran 4.0 g (11.7 mmole) of one of the compounds obtained in step 4, having higher $R_f$ value was dissolved in 50 ml of dioxane-water (5:1); and, 0.94 g (23.4 mmole) of sodium hydroxide was added thereto at room temperature. After the resultant mixture was stirred for 30 minutes, the solvent was distilled under reduced pressure. The residue so obtained was extracted with ethyl acetate (100 ml×2), washed with 50 ml of water and with 50 ml of a sodium chloride solution, dried over anhydrous magnesium sulfate and concentrated to obtain 2.69 g (yield 88%) of the desired compound in the form of a white solid.

$^1$H NMR(CDCl$_3$, 300 MHz) δ1.25(s, 3H, CH$_3$), 3.58(s, 3H, OCH$_3$), 3.65(s, 3H, OCH$_3$), 3.75(d, 1H, H-3), 3.88(d, 1H, H-4), 4.2(s, 1H), 6.9(d, 1H, H-8), 7.52(dd, 1H, H-5), 7.68(d, 1H, H-7).

PREPARATION EXAMPLE 2

Synthesis of 2-dimethoxymethyl-2-methyl-3,4-epoxy-6-nitro-3,4-dihydro-2H-1-benzopyran Step 1) Synthesis of 2-dimethoxymethyl-2-methyl-4-oxo-3,4-dihydro-2H-1-benzopyran In 250 ml of toluene were dissolved 30 g (0.22 mmole) of 2-hydroxy acetophenone and 33.8 g (0.29 mmole) of pyruvic aldehyde dimethyl acetal; and 6.3 g (0.09 mmole) of pyridine was added thereto. After stirring at room temperature 30 minutes, the reactants were heated to reflux for 5 hours, using Dean-Stark apparatus. The solvent was removed under reduced pressure; and 100 ml of 2N HCl aqueous solution was added thereto. The resultant solution was stirred for 1 hour at room temperature, extracted with ethyl acetate (200 ml×2), and washed with 100 ml of water and with 50 ml of saturated sodium chloride aqueous solution; and purified by silica gel column chromatography using a mixture of hexane and ethyl acetate (4:1) as an eluent to obtain 39 g (0.16 mmole, yield 75%) of the title compound in the form of a white solid.

Step 2) Synthesis of 2-dimethoxymethyl-2-methyl-4-oxo-6-nitro-3,4-dihydro-2H-1-benzopyran In 15 ml of chloroform were dissolved 1.9 g (8.1 mmole) of the compound obtained in step 1 and 0.64 g (8.1 mmole) of ammonium nitrate; and, 4.5 ml (32 mmole) of anhydrous trifluoroacetic acid was added thereto at room temperature. The resultant mixture was stirred at room temperature for 3 hours; and the reaction was terminated by addition of 10 ml of saturated NaHCO$_3$ aqueous solution. The resultant solution was extracted with dichloromethane (50 ml×2), washed with 50 ml of water and with 20 ml of saturated sodium chloride solution, dried over anhydrous magnesium sulfate, and filtered and concentrated. The residue so obtained was purified by silica gel column chromatography using a mixture of hexane and ethyl acetate (4:1) as an eluent to obtain 1.24 g (yield 55%) of the title compound.

Step 3) Synthesis of 2-dimethoxymethyl-2-methyl-4-hydroxy-6-nitro-3,4-dihydro-2H-1-benzopyran In 8 ml of methanol was dissolved 726 mg (2.6 mmole) of the compound obtained in the step 2; and, 98 mg (2.6 mmole) of sodium borohydride was slowly added thereto. After the reaction mixture was stirred at 0° C. for 1 hour, methanol was removed therefrom under reduced pressure; and 20 ml of water was added to the residue so obtained. The resultant solution was extracted with 50 ml of ethyl acetate, washed with 10 ml of saturated sodium chloride solution, dried over anhydrous magnesium sulfate, filtered and evaporated under reduced pressure to obtain 620 mg (yield 85%) of the title compound.

Step 4) Synthesis of 2-dimethoxymethyl-2-methyl-6-nitro-2H-1-benzopyran

In 100 ml of chloroform was dissolved 6.13 g (22 mmole) of the compound obtained in step 3; and, 7.5 ml (43 mmole) of N,N-diisopropylethylamine and 2.5 ml (32 mmole) of methanesulfonyl chloride were added thereto. The resultant solution was stirred for 15 hours at room temperature, diluted with 100 ml of chloroform, and washed with 100 ml of water and 100 ml of saturated sodium chloride solution. The organic layer was dried over anhydrous magnesium sulfate, filtered and evaporated to obtain a mixture of the desired compound and a chloride. The mixture was dissolved in 30 ml of toluene again; and 4.95 g (32 mmole) of DBU was added thereto. The resultant solution was heated to reflux for 5 hours and evaporated under reduced pressure to remove toluene solvent. The residue so obtained was extracted with ethyl acetate (100 ml×2), and washed with 80 ml of water and with 50 ml of saturated sodium chloride solution. The organic layer was dried over anhydrous magnesium sulfate, filtered and concentrated under reduced pressure to obtain residue, which was purified by silica gel column chromatography using a mixture of hexane and ethyl acetate (4:1) as an eluent to obtain 4.03 g (yield 70%) of the title compound.

Step 5) Synthesis of 2-dimethoxymethyl-2-methyl-3-bromo-4-hydroxy-6-nitro-3,4-dihydro-2H-1-benzopyran In 10 ml of DMSO was dissolved 1.79 g (6.8 mmole) of the compound obtained in step 4; and, 0.24 ml (13.5 mmole) of water and 2.41 g (13.5 mmole) of N-bromosuccinimide were added at room temperature.

The resultant solution was stirred at room temperature for 2 hours, diluted with 20 ml of water, washed with ethyl acetate (30 ml×2), dried over anhydrous magnesium sulfate, filtered and concentrated under reduced pressure to obtain residue, which was purified by silica gel column chromatography using a mixture of hexane and ethyl acetate (4:1) as an eluent to obtain 0.42 g (yield 17%) and 0.59 g (yield 24%) of each of diastereomers of the title compound.

Step 6) Synthesis of 2-dimethoxymethyl-2-methyl-3,4-epoxy-6-nitro-3,4-dihydro-2H-1-benzopyran 0.48 g (1.3 mmole) of one of the compounds obtained in step 5 having higher $R_f$ value was dissolved in 5 ml of dioxane-water (5:1); and, 100 mg (2.6 mmole) of sodium hydroxide was added thereto at room temperature. After the resultant mixture was stirred for 2 hours, the solvent was distilled off under reduced pressure. The residue so obtained was extracted with ethyl aceate (20 ml×2), washed with 10 ml of water and with 10 ml of saturated sodium chloride solution, dried over anhydrous magnesium sulfate, filtered and concentrated to obtain 0.35 g (yield 94%) of the desired compound.

$^1$H NMR(CDCl$_3$, 300 MHz) δ1.30(s, 3H, CH$_3$), 3.6(s, 3H, OCH$_3$), 3.7(s, 3H, OCH$_3$), 3.82(d, 1H, H-3), 4.0(d, 1H, H-4), 4.20(s, 1H), 7.0(d, 1H, H-8), 8.2(dd, 1H, H-5), 8.35(d, 1H, H-7).

PREPARATION EXAMPLE 3

Synthesis of 2-dimethoxymethyl-2-methyl-3,4-epoxy-6-phenylsulfonyl-2H-1-benzopyran Step 1) Synthesis of 4-phenylsulfonyl-1-methoxybenzene To a solution of 16 g of AlCl$_3$ dissolved in 21.6 g of anisol was added dropwise 17.6 g of benzenesulfonyl chloride. The reaction mixture was heated to reflux for 8 hours and poured into 1N HCl solution containing ice. The resultant solution was extracted with ethyl acetate (100 ml×3), washed with 100 ml of saturated NaHCO$_3$ aqueous solution, dried over Na$_2$SO$_4$ and concentrated to obtain residue, which was recrystallized from hexane-ethyl acetate to obtain 25 g of the title compound.

Step 2) Synthesis of 4-phenylsulfonyl-1-hydroxybenzene

To a solution of 24.8 g (100 mmole) of the compound obtained in step 1 dissolved in 50 ml of acetic acid was added 40% HBr, which was heated to reflux for 8 hours. The reaction solution was poured into ice-water. The resultant solution was extracted with ethyl acetate (100 ml×3), dried over Na$_2$SO$_4$ and concentrated to obtain residue, which was purified by silica gel column chromatography using a mixture of hexane and ethyl acetate (1:1) as an eluent to obtain 23.0 g (yield 100%) of the title compound containing a portion of ortho-isomer (approximately one-eighth).

Step 3) Synthesis of 4-phenylsulfonyl-1-acetoxybenzene

In 150 ml of CH$_2$Cl$_2$ were dissolved 23 g of the compound obtained in step 2; and, 12.9 ml of pyridine and 7.8 ml of acetyl chloride was slowly added thereto at room temperature. The reaction solution was washed with 0.2N HCl and with saturated NaHCO$_3$ aqueous solution, dried over Na$_2$SO$_4$ and concentrated under reduced pressure to obtain residue, which was used for subsequent reaction without further purification.

Step 4) Synthesis of 4-phenylsulfonyl-2-acetylphenol

To a solution of 0.67 g of the compound obtained in step 3 dissolved in 5 ml of CS$_2$ was added 0.97 g of AlCl$_3$. The reaction mixture was heated to the temperature of 190° C. (at this temperature, CS$_2$ would be distilled) and maintained at that temperature for 30 minutes. The reaction mixture was poured into 1N HCl solution containing ice. The resultant solution was extracted with ethyl aceate (20 ml×3), dried over Na$_2$SO$_4$ and concentrated under reduced pressure to obtain residue, which was purified by silica gel column chromatography using a mixture of hexane and ethyl acetate (2:1) as an eluent to obtain 0.35 g (yield 52%) of the title compound.

Step 5) Synthesis of 2-dimethoxymethyl-2-methyl-4-oxo-6-phenylsulfonyl-3,4-dihydro-2H-1-benzopyran In 100 ml of toluene were dissolved 10 g of the compound obtained in step 4, 6.5 ml of pyruvic aldehyde dimethyl acetal and 1.5 ml of pyrrolidine. The resultant solution was heated to reflux for 16 hours and concentrated under reduced pressure to obtain residue, which was purified by silica gel column chormatography using a mixture of hexane and ethyl acetate (2:1) to obtain 11 g of the title compound.

Step 6) Synthesis of 2-dimethoxymethyl-2-methyl-4-hydroxy-6-phenylsulfonyl-3,4-dihydro-2H-1-benzopyran To a solution of 6 g of the compound obtained in the step 5 dissolved in 50 ml of methanol was added 1.74 g (1.2 eq.) of sodium borohydride (NaBH$_4$). After stirring, methanol was removed from the reaction mixture under reduced pressure to give residue, which was dissolved in 100 ml of CH$_2$Cl$_2$. The resultant solution was washed with 50 ml of distilled water and with 30 ml of saturated sodium chloride aqueous solution, dried over Na$_2$SO$_4$ and concentrated to obtain residue, which was used for subsequent reaction without further purification.

Step 7) Synthesis of 2-dimethoxymethyl-2-methyl-6-phenylsulfonyl-2H-1-benzopyran To the mixture of the compound obtained in step 6 and 1.1 ml of diisopropylethylamine was added 1.1 ml of methanesulfonyl chloride. The resultant solution was stirred for 16 hours at room temperature, washed with saturated sodium chloride solution and concentrated to give residue. To this was added a solution of 1.6 g of DBU dissolved in 20 ml of toluene. The resultant solution was heated to reflux for 6 hours and concentrated under reduced pressure to obtain residue, which was purified by silica gel column chromatography using a mixture of hexane and ethyl acetate (1:1) to obtain 3 g of the title compound.

Step 8) Synthesis of 2-dimethoxymethyl-2-methyl-3,4-epoxy-6-phenylsulfonyl-3,4-dihydro-2H-1-benzopyran To a solution of 3 g (8.72 mmole) of the compound obtained in step 7 dissolved in a mixture of 10 ml of acetone and 10 ml of distilled water was added 2.2 g (26.16 mmole) of NaHCO$_3$. 5.45 g (8.72 mmole) of oxon was added at once thereto. After stirring for 10 minutes, NaHCO$_3$ and oxon were further added in same manner as described above. The resultant mixture was stirred for about 20 minutes. The mixture was distilled under reduced pressure to remove acetone solvent, extracted with ethyl acetate (30 ml×3) and concentrated. The residue obtained was purified silica gel column chromatography using a mixture of hexane and ethyl acetate (1:1) as an eluent to obtain 2.5 g (yield 80%) of the desired compound.

$^1$H NMR(CDCl$_3$, 200 MHz) δ1.28(s, 3H), 3.60(s, 3H), 3.70(s, 3H), 3.82(d, 1H), 4.0(d, 1H), 4.25(s, 1H), 6.80(d, 1H), 7.20 (d, 1H), 7.40(dd, 1H), 7.45(m, 5H)

PREPARATION EXAMPLE 4

Synthesis of 2-dimethoxymethyl-2-methyl-3,4-epoxy-6-trifluoromethoxy-2H-1-benzopyran Step 1) Synthesis of 4-trifluoromethoxy-2-(α-hydroxyethyl)phenol To a solution of 1.0 g (4.85 mmole) of 5-(trifluoromethoxy) salicyl aldehyde dissolved in 500 ml of dry ether was slowly added 10.34 ml (14.55 mmole) of 1.4M CH$_3$Li at room temperature. The resultant solution was stirred for 30 minutes at room temperature; and, 1N HCl was added thereto to acidify the solution. The acidified solution was extracted with ethyl acetate (20 ml×3), dried and concentrated to obtain residue, which was purified by silica gel column chromatography using a mixture of hexane and ethyl acetate (2:1) obtain the 0.88 g (yield 82%) of title compound.

$^1$H NMR(CDCl$_3$, 200 MHz) δ1.6 (d, 3H), 2.6(d, 1H), 5.1(m, 1H), 6.85 (m, 2H), 7.1(m, 1H), 8.1(s, 1H).

Step 2) Synthesis of 4-trifluoromethoxy-2-acetylphenol

In 20 ml of dichloromethane was dissolved 0.85 g (3.83 mmole) of the compound obtained in step 1; and, a suitable amount of Cellite and 1.73 g (4.6 mmole) of pyridinium dichromate were added thereto. The resultant mixture was stirred for 30 minutes at room temperature and filtered by a Cellite layer to obtain precipitates, which were purified by silica gel column chromatography using a mixture of hexane and ethyl acetate (6:1); and, then concentrated under reduced pressure at 0° C. to obtain 0.72 g (yield 85%) of the title compound.

Step 3) Synthesis of 2-dimethoxymethyl-2-methyl-4-oxo-6-trifluoromethoxy-3,4-dihydro-2H-1-benzopyran To a solution of 0.5 g (2.27 mmole) of the compound obtained in step 2 dissolved in 10 ml of toluene were added 0.55 ml (4.54 mmole) of pyruvic aldehyde dimethyl acetal and 80 mg (1.14 mmole) of pyrrolidine. The reactants were heated to reflux for about 12 hours using Dean-Stark apparatus. After completion of the reaction, toluene solvent was removed therefrom under reduced pressure. The residue so obtained was extracted with ethyl acetate and concentrated to give residue, which was purified by silica gel column chromatography using a mixture of hexane and ethyl acetate (10:1) as an eluent to provide 0.470 g (yield 65%) of the title compound.

$^1$H NMR (CDCl$_3$, 200 MHz) δ1.4(s, 3H), 2.6~2.7(d, 1H), 3.0~3.1(d, 1H), 3.5(d, 6H), 4.3(s, 1H), 7.0(d, 1H), 7.3(q, 1H), 7.7(q, 1H).

Step 4) Synthesis of 2-dimethoxymethyl-2-methyl-4-hydroxy-6-trifluoromethoxy-3,4-dihydro-2H-1-benzopyran In 3 ml of methanol was dissolved 0.22 g (0.69 mmole) of the compound obtained in the step 3; and, 31 mg (0.83 mmole) of sodium borohydride was added thereto. After stirring at room temperature for 1 hour, the resultant solution was extracted with ethyl acetate (20 ml×3), and washed with saturated sodium chloride aqueous solution (10 ml×2). The organic layer was dried over anhydrous Na$_2$SO$_4$, and concentrated; and, purified by silica gel column chromatography using a mixture of hexane and ethyl acetate (3:1) to obtain 0.18 g (0.56 mmole) (yield 81%) of the title compound.

Step 5) Synthesis of 2-dimethoxymethyl-2-methyl-6-trifluoromethoxy-2H-1-benzopyran In 1 ml of dichloromethane was dissolved 69 mg (0.214 mmole) of the compound obtained in step 4; and, 75 μl (0.742 mmole) of N,N-diisopropylethylamine and 25 μl (0.321 mmole) of methanesulfonyl chloride were added thereto. The resultant solution was stirred for 15 hours at room temperature, diluted with 10 ml of dichloromethane and washed with 10 ml of water and then with 10 ml of saturated sodium chloride solution. The organic layer was dried over anhydrous magnesium sulfate, filtered and evaporated under reduced pressure to obtain a mixture of the desired compound and a chloride. The mixture was dissolved in 2 ml of toluene again; and, 48 μl (0.321 mmole) of DBU was added. The resultant solution was heated to reflux for 6 hours and evaporated under reduced pressure to remove toluene. The residue obtained was extracted with ethyl acetate (10 ml×2), washed with 5 ml of water and with 5 ml of saturated sodium chloride solution, dried over anhydrous magnesium sulfate, filtered and concentrated under reduced pressure to obtain residue, which was purified by silica gel column chromatography using a mixture of hexane and ethyl acetate (4:1) to obtain 40 mg (yield 61%) of the title compound.

Step 6) Synthesis of 2-dimethoxymethyl-2-methyl-3,4-epoxy-6-trifluoromethoxy-3,4-dihydro-2H-1-benzopyran To a solution of 32 mg (0.105 mmole) of the compound obtained in step 5 dissolved in a mixture of 1 ml of acetone and 1 ml of distilled water were added by three steps 31 mg (0.368 mmole) of NaHCO$_3$ and 65 mg (0.105 mmole) of oxon. After stirring at room temperature for 1 hour, the reaction was completed. Acetone solvent was removed under reduced pressure to give residue, which was extracted with ethyl acetate (5 ml×3) and washed with 5 ml of water and with 5 ml of saturated sodium chloride solution. The organic layer was dried over MgSO$_4$, filtered and concentrated under reduced pressure. The residue obtained was purified by silica gel column chromatography using a mixture of hexane and ethyl acetate (4:1) as an eluent to obtain 16 mg (yield 48%) of the desired compound.

$^1$H NMR (CDCl$_3$, 300 MHz) δ1.5(s, 3H, CH$_3$), 3.6(d, 6H, (OCH$_3$)$_2$), 3.9(d, 1H, H-3), 4.1(d, 1H, H-4), 4.3(s, 1H, CH(OCH$_3$)$_2$), 6.8(d, 1H, aromatic), 6.92(d, 1H, aromatic), 7.1(dd, 1H, aromatic).

EXAMPLE 1

Synthesis of 2-dimethoxymethyl-2-methyl-4-(2'-oxo-1'-pyrrolidinyl)-6-cyano-2H-1-benzopyran Step 1) Synthesis of 2-dimethoxymethyl-2-methyl-3-hydroxy-4-(2'-oxo-1'-pyrrolidinyl)-6-cyano-3,4-dihydro-2H-1-benzopyran To a solution of 0.59 g (6.9 mmole) of 2-pyrrolidine dissolved in 15 ml of t-butanol was added 10.77 g (6.9 mmole) of potassium t-butoxide. The reaction mixture was stirred at room temperature for 20 minutes; and 1.2 g (4.6 mmole) of the compound obtained in Preparation Example 1 was added thereto. The resultant mixture was stirred at room temperature for 24 hours; and the reaction was terminated with 5 ml of water. The resultant mixture was extracted with ethyl acetate (30 ml×2), washed with 30 ml of water and then with 30 ml of saturated sodium chloride solution, dried over anhydrous magnesium sulfate, filtered and concentrated to obtain 1.39 g (yield 87%) of the title compound in the form of a white solid.

$^1$H NMR (CDCl$_3$, 300 MHz) δ1.4(s, 3H, CH$_3$), 2.1(m, 2H, NCH$_2$CH$_2$), 2.6(t, 2H, NCOCH$_2$), 3.08(m, 1H, NCH$_2$), 3.45(m, 1H, NCH$_2$), 3.62(d, 6H, (OCH$_3$)$_2$), 3.85(m, 1OH), 4.24(d, 1H, H-3), 4.45(s, 1H, CH(OCH$_3$)$_2$), 5.3(d, 1H, H-4), 6.95(d, 1H, H-8), 7.3(d, 1H, H-5), 7.47(dd, 1H, H-7).

Step 2) Synthesis of 2-dimethoxymethyl-2-methyl-4-(2'-oxo-1'-pyrrolidinyl)-6-cyano-2H-1-benzopyran To a solution of 80 mg (0.24 mmole) of the compound obtained in step 1 dissolved in 1 ml of DMF was added 10 mg (0.24 mmole) of sodium hydride (60%) at room temperature. After stirring at room temperature for 24 hours, the reaction was terminated by addition of 10 ml of water. The reaction mixture was extracted with 10 ml of ethyl acetate, washed with 5 ml of saturated sodium chloride solution, dried over anhydrous magnesium sulfate and concentrated to obtain residue; and the residue was purified by silica gel column chromatography using a mixture of hexane and ethyl acetate (1:1) as an eluent to obtain 39 mg (yield 51%) of the desired compound.

$^1$H NMR (CDCl$_3$, 300 MHz) δ1.41(s, 3H, CH$_3$), 2.2(m, 2H, NCH$_2$CH$_2$), 2.52(t, 2H, NCOCH$_2$), 3.45(d, 6H, (OCH$_3$)$_2$), 3.6(+, 2H, NCH$_2$), 4.23(s, 1H, CH(OCH$_3$)$_2$), 5.7(s, 1H, H-3), 6.85(d, 1H, H-8), 7.18(d, 1H, H-5), 7.39(dd, 1H, H-7).

EXAMPLE 2

Synthesis of 2-dimethoxymethyl-2-methyl-4-(2'-oxo-1'-pyrrolidinyl)-6-nitro-2H-1-benzopyran Step 1) Synthesis of 2-dimethoxymethyl-2-methyl-3-hydroxy-4-(2'-oxo-1'-pyrrolidinyl)-6-nitro-3,4-dihydro-2H-1-benzopyran To a solution of 63 μl (0.83 mmole) of 2-pyrrolidine dissolved in 2 ml of t-butanol was added 93 mg (0.83 mmole) of potassium t-butoxide. The reaction mixture was stirred at room temperature for 20 minutes; and 155 mg (0.55 mmole) of the compound obtained in Preparation Example 2 was added thereto. The resultant mixture was stirred at room temperature for 24 hours; and, the reaction was terminated by addition of 10 ml of water. The resultant mixture was extracted with ethyl acetate (20 ml×2), washed with 10 ml of water and with 10 ml of saturated sodium chloride solution, dried over anhydrous magnesium sulfate, filtered, concentrated and recrystallized from ethers/hexane to obtain 96 mg (yield 47%) of the title compound in the form of a white solid.

Step 2) Synthesis of 2-dimethoxymethyl-2-methyl-4-(2'-oxo-1'-pyrrolidinyl)-6-nitro-2H-1-benzopyran To a solution of 44 mg (0.12 mmole) of the compound obtained in step 1 dissolved in 1 ml of dioxane was added 10 mg (0.24 mmole) of sodium hydride (60%) at room temperature. After stirring at room temperature for 24 hours, the reaction was terminated by addition of 10 ml of water. The reaction mixture was extracted with ethyl acetate (10 ml×2), washed with 10 ml of saturated sodium chloride solution, dried over anhydrous magnesium sulfate and concentrated to obtain residue, which was purified by silica gel column chromatography using a mixture of hexane and ethyl acetate (1:1) as an eluent to obtain 30 mg (yield 92%) of the desired compound.

$^1$H NMR (CDCl$_3$, 300 MHz) δ1.55(s, 3H, CH$_3$), 2.3(m, 1H, NCOCH$_2$CH$_2$), 2.62(t, 1H, NCOCH$_2$), 3.65(m, 1H, NCH$_2$), 4.0(d, 6H, (OCH$_3$)$_2$), 5.0(s, 1H, CHC(OCH$_3$)$_2$), 5.7(s, 1H, H-3), 6.9(d, 1H, H-8), 7.8(d, 1H, H-5), 8.1(dd, 1H, H-7).

EXAMPLE 3

Synthesis of 2-dimethoxymethyl-2-methyl-4-(2'-oxo-1'-pyrrolidinyl)-6-phenylsulfonyl-2H-1-benzopyran In accordance with the procedures described in Example 1 above, the title compound was prepared using the compound obtained in Preparation Example 3 and purified by column chromatography.

$^1$H NMR(CDCl$_3$, 300 MHz) δ1.41(s, 3H), 2.2(m, 2H), 2.6(t, 2H), 3.30(s, 3H), 3.32(s, 3H), 3.6(t, 2H), 4.25(s, 1H), 5.7(s, 1H), 6.80(d, 1H), 7.18(d, 1H), 7.39(dd, 1H), 7.45(m, 5H).

EXAMPLE 4

Synthesis of 2-dimethoxymethyl-2-methyl-4-(2'-oxo-1'-pyrrolidinyl)-6-trifluoromethoxy-2H-1-benzopyran In accordance with the procedures described in Example 1 above, the title compound was prepared using the compound obtained in Preparation Example 4 and purified by column chromatography.

$^1$H NMR(CDCl$_3$, 200 MHz) δ1.50(s, 3H), 3.30(s, 3H), 3.32(s, 3H), 4.30(s, 1H), 5.70(s, 1H), 6.75(t, 1H), 6.85(d, 1H), 7.0(dd, 1H).

EXAMPLE 5

Synthesis of 2-dimethoxymethyl-2-methyl-4-(1'-(2'-oxo-1',2'-dihydropyridyl))-6-cyano-2H-1-benzopyran In accordance with the procedures described in Example 1 above, the title compound was prepared using the compound obtained in Preparation Example 1 and 2-oxo-1,2-dihydropyridine as starting materials and purified by column chromatography.

$^1$H NMR(CDCl$_3$, 300 MHz) δ1.41(s, 3H), 3.43(s, 3H), 3.45(s, 3H), 4.39(s, 1H), 5.80(s, 1H), 6.23(td, 1H), 6.63(d, 1H), 6.80(dd, 1H), 6.95(d, 1H), 7.10(s, 1H), 7.38(td, 1H), 7.45(dd, 1H).

EXAMPLE 6

Synthesis of 2-dimethoxymethyl-2-methyl-4-(1'-(2'-oxo-1',2'-dihydropyridyl))-6-nitro-2H-1-benzopyran In accordance with the procedures described in Example 5 above, the title compound was prepared using the compound obtained in Preparation Example 2 and purified by column chromatography.

$^1$H NMR(CDCl$_3$, 300 MHz) δ1.40(s, 3H), 3.42(s, 3H), 3.40(s, 3H), 4.30(s, 1H), 5.90(s, 1H), 6.20(td, 1H), 6.65(d, 1H), 6.85(dd, 1H), 7.0(d, 1H), 7.40(dt, 1H), 7.80(d, 1H), 8.1(dd, 1H).

EXAMPLE 7

Synthesis of 2-(2''-(1'',3''-dioxolane))-2-methyl-4-(2'-oxo-1'-pyrrolidinyl)-6-cyano-2H-1-benzopyran Step 1) Synthesis of 2-(2''-(1'',3''-dioxolane))-2-methyl-3-hydroxy-4-(2'-oxo-1'-pyrrolidinyl)-6-cyano-3,4-dihydro-2H-1-benzopyran To a solution of 0.05 g (0.1445 mmole) of the compound obtained in step 1 of Example 1 above dissolved in 5 ml of toluene were added 17.9 mg (0.2890 mmole) of ethylene glycol and 5.7 mg (0.03 mmole) of p-toluene sulfonic acid. The reaction mixture was heated to reflux for 1 hour with Dean-Stark apparatus. The reaction mixture was cooled to room temperature after completion of the reaction, extracted with ethyl acetate (5 ml×3), washed with 5 ml of water and with 5 ml of saturated sodium chloride solution, dried over MgSO$_4$, filtered and concentrated. The residue obtained was purified by silica gel column chromatography using a mixture of hexane and ethyl acetate (1:4) as an eluent to obtain 0.049 g (0.142 mmole) (yield 99%) of the title compound in the form of a white solid.

Step 2) Synthesis of 2-(2″-(1″,3″-dioxolane))-2-methyl-4-(2′-oxo-1′-pyrrolidinyl)-6-cyano-2H-1-benzopyran To a solution of 0.05 g (0.15 mmole) of the compound obtained in step 1 dissolved in 5 ml of dioxane was added 12 mg (0.29 mmole) of NaOH. The reaction mixture was heated to reflux for 30 minutes and cooled to room temperature after completion of the reaction. The dioxane solvent was removed therefrom under reduced pressure. The residue obtained was extracted with 20 ml of CH$_2$Cl$_2$, washed with 10 ml of water and with 5 ml of saturated sodium chloride solution, dried over MgSO$_4$, filtered and concentrated to obtain residue, which was purified by silica gel column chromatography using a mixture of hexane and ethyl acetate of (1:4) as an eluent and recrystallized several times from ethers to obtain 42 mg (0.13 mmole, yield 89%) of the desired compound in the form of a white solid.

$^1$H NMR(CDCl$_3$, 300 MHz) δ1.55(s, 3H, CH$_3$), 2.25(m, 2H, NCH$_2$CH$_2$), 2.61(t, 2H, NCOCH$_2$), 3.65(m, 2H, NCH$_2$), 4.0(m, 4H, —OCH$_2$CH$_2$O—), 4.98(s, 1H, CHCOCH$_2$), 5.67(s, 1H, H-3), 6.88(d, 1H, H-8), 7.16(d, 1H, H-5), 7.42(dd, 1H, H-7).

EXAMPLE 8

Synthesis of 2-(2″-(1″,3″-dioxolane))-2-methyl-4-(2′-oxo-1′-pyrrolidinyl)-6-nitro-2H-1-benzopyran Step 1) Synthesis of 2-(2″-(1″,3″-dioxolane))-2-methyl-3-hydroxy-4-(2″-oxo-1′-pyrrolidinyl)-6-nitro-3,4-dihydro-2H-1-benzopyran To a solution of 0.051 g (0.14 mmole) of the compound obtained in step 1 of Example 2 above dissolved in 5 ml of toluene were added 17.3 mg (0.28 mmole) of ethylene glycol and 5.7 mg (0.03 mmole) of p-toluene sulfonic acid. The reaction mixture was heated to reflux for 1 hour with Dean-Stark apparatus. The reaction mixture was cooled to room temperature after completion of the reaction, extracted with ethyl acetate (5 ml×3), washed with 5 ml of water and with 5 ml of saturated sodium chloride solution, dried over MgSO$_4$, filtered and concentrated. The residue obtained was purified by silica gel column chromatography using a mixture of hexane and ethyl acetate (1:4) as an eluent to obtain 48 mg (0.13 mmole) (yield 95%) of the title compound in the form of a white solid.

Step 2) Synthesis of 2-(2″-(1″,3″-dioxolane))-2-methyl-4-(2′-oxo-1′-pyrrolidinyl)-6-nitro-2H-1-benzopyran To a solution of 0.048 g (0.13 mmole) of the compound obtained in step 1 dissolved in 5 ml of dioxane was added 10.6 mg (0.26 mmole) of NaOH. The reaction mixture was heated to reflux for 30 minutes and cooled to room temperature after completion of the reaction. The dioxane solvent was removed therefrom under reduced pressure. The residue obtained was extracted with 20 ml of CH$_2$Cl$_2$, washed with 10 ml of water and with 5 ml of saturated sodium chloride solution, dried over MgSO$_4$, filtered and concentrated to obtain residue, which was purified by silica gel chromatography using a mixture of hexane and ethyl acetate (1:4) as an eluent and recrystallized several times from ethers to obtain 42 mg (0.13 mmole, yield 89%) of the desired compound in the form of a white solid.

$^1$H NMR(CDCl$_3$, 300 MHz) δ1.55(s, 3H, CH$_3$), 2.3(m, 2H, NCH$_2$CH$_2$), 2.61(t, 2H, NCOCH$_2$), 3.67(m, 2H, NCH$_2$), 4.0(m, 4H, —OCH$_2$CH$_2$O—), 5.0(s, 1H, CHOCH$_2$), 5.7(s, 1H, H-3), 6.9(d, 1H, H-8), 7.85(d, 1H, H-5), 8.1(dd, 1H, H-7)

EXAMPLE 9

Synthesis of 2-(2″-(1″,3″-dioxolane))-2-methyl-4-(2′-oxo-1′-pyrrolidinyl)-6-trifluoromethoxy-2H-1-benzopyran Step 1) Synthesis of 2-dimethoxymethyl-2-methyl-3-hydroxy-4-(2′-oxo-1′-pyrrolidinyl)-6-trifluoromethoxy-3,4-dihydro-2H-1-benzopyran To a solution of 5.3 μl (0.07 mmole) of 2-pyrrolidone dissolved in 1 ml of t-butanol was added 7.9 mg (0.07 mmole) of potassium t-butoxide. After stirring at room temperature for 20 minutes, 15 mg (0.0047 mmole) of the epoxide obtained in Preparation Example 4 above was added. The reaction mixture was stirred at room temperature for 24 hours; and, the reaction was terminated by addition of water. The resultant solution was extracted with ethyl acetate (5 ml×3), washed with 5 ml of water and with 5 ml of saturated sodium chloride solution, dried over MgSO$_4$, filtered and concentrated to obtain 10 mg (yield 53%) of the title compound.

Step 2) Synthesis of 2-(2″-(1″,3″-dioxolane))-2-methyl-3-hydroxy-4-(2′-oxo-1′-pyrrolidinyl)-6-trifluoromethoxy-3,4-dihydro-2H-1-benzopyran To a solution of 10 mg (0.025 mmole) of the compound obtained in step 1 dissolved in 1 ml of toluene were added 2.5 μl (0.05 mmole) of ethylene glycol and a catalytic amount of p-toluene sulfonic acid. The reaction mixture was heated to reflux. 1 Hour thereafter, the reaction mixture was extracted with ethyl acetate (5 ml×3), washed with 5 ml of saturated sodium chloride solution, dried over MgSO$_4$, and concentrated under reduced pressure. The residue so obtained was purified by silica gel column chromatography using a mixture of hexane and ethyl acetate (1:4) as an eluent to obtain 9 mg (yield 89%) of the title compound.

Step 3) Synthesis of 2-(2″-(1″,3″-dioxolane))-2-methyl-4-(2′-oxo-1′-pyrrolidinyl)-6-trifluoromethoxy-2H-1-benzopyran To a solution of 9 mg (0.022 mmole) of the compound obtained in step 2 dissolved in 1 ml of dioxane was added 2 mg (0.044 mmole) of NaOH. The reaction mixture was heated to reflux for 1 hour. After completion of the reaction, the dioxane solvent was removed therefrom under reduced pressure. The residue so obtained was extracted with CH$_2$Cl$_2$ (5 ml×2), washed with 5 ml of water and with 5 ml of saturated sodium chloride solution, dried over MgSO$_4$, filtered and concentrated under reduced pressure. The residue so obtained was purified by silica gel column chromatography using a mixture of hexane and ethyl acetate (1:4) as an eluent to obtain 52 mg (yield 60%) of the desired compound.

$^1$H NMR(CDCl$_3$, 300 MHz) δ1.5(s, 3H, CH$_3$), 2.2(m, 2H, NCOCH$_2$), 3.65(t, 2H, NCOCH$_2$CH$_2$CH$_2$), 3.95(m, 2H, OCH$_2$), 4.05(m, 2H, OCH$_2$), 5.05(s, 1H,

C(OCH$_2$)$_2$), 5.7(s, 1H, H-3), 6.75(d, 1H, aromatic), 6.85(d, 1H, aromatic), 7.0(dd, 1H, aromatic).

EXAMPLE 10

Synthesis of 2-(2''-(1'',3''-dioxane))-2-methyl-4-(2'-oxo-1'-pyrrolidinyl)-6-cyano-2H-1-benzopyran In accordance with the procedures described in Example 7 above, the title compound was prepared using 2-dimethoxymethyl-2-methyl-3-hydroxy-4-(2'-oxo-1'-pyrrolidinyl)-6-cyano-3,4-dihydro-2H-1-benzopyran obtained in step 1 of Example 1 above and 1,3-propanediol as starting materials and then purified by column chromatography.

$^1$H NMR(CDCl$_3$, 300 MHz) δ1.35(m, 2H, OCH$_2$CH$_2$), 1.5(s, 3H, CH$_3$), 2.3(m, 1H, NCH$_2$CH$_2$), 2.6(m, 1H, NCOCH$_2$), 3.75(m, 1H, OCH$_2$, 1H, NCH$_2$), 4.2(m, 1H, OCH$_2$), 4.7(s, 1H, CH(OCH$_2$)$_2$CH$_2$), 5.85(s, 1H, H-3), 6.98(d, 1H, H-8), 7.25(d, 1H, H-5), 7.48(dd, 1H, H-7).

EXAMPLE 11

Synthesis of 2-(2''-(1'',3''-dioxane))-2-methyl-4-(2'-oxo-1'-pyrrolidinyl)-6-nitro-2H-1-benzopyran Similarly to Example 10 above, the title compound was prepared using the compound obtained in step 1 of Example 2 above and then purified by column chromatography.

$^1$H NMR(CDCl$_3$, 300 MHz) δ1.4(m, 2H, OCH$_2$CH$_2$), 1.5(s, 3H, CH$_3$), 2.3(m, 1H, NCH$_2$CH$_2$), 2.85(m, 1H, NCOCH$_2$), 3.75(m, 1H, OCH$_2$, 1H, NCH$_2$), 4.2(m, 1H, OCH$_2$), 4.7(s, 1H, CH(OCH$_2$)$_2$CH$_2$), 5.9(s, 1H, H-3), 6.9(d, 1H, H-8), 7.89(d, 1H, H-5), 8.1(dd, 1H, H-7).

EXAMPLE 12

Synthesis of 2-(2''-(1'',3''-dioxolane))-2-methyl-4-(1'-(2'-oxo-1',2'-dihydropyridyl))-6-cyano-2H-1-benzopyran In accordance with the procedures described in Example 7 above, the title compound was prepared using 2-dimethoxy-methyl-2-methyl-3-hydroxy-4-(1'-(2'-oxo-1',2'-dihydropyridyl))-6-cyano-3,4-dihydro-2H-1-benzopyran obtained in the course of Example 5 above and then purified by column chromatography.

$^1$H NMR(CDCl$_3$, 300 MHz) δ1.54(s, 3H), 3.80(m, 2H), 3.90(m, 2H), 4.23(s, 1H), 5.80(s, 1H), 6.25(td, 1H), 6.63(d, 1H), 6.87(dd, 1H), 7.00(d, 1H), 7.15(d, 1H), 7.38(td, 1H), 7.50(dd, 1H).

EXAMPLE 13

Synthesis of 2-(2''-(1'',3''-dioxane))-2-methyl-4-(1'-(2'-oxo-1',2'-dihydropyridyl))-6-cyano-2H-1-benzopyran Similarly to Example 10 above, the title compound was prepared using 2-dimethoxy-methyl-2-methyl-3-hydroxy-4-(1'-(2'-oxo-1',2'-dihydropyridyl))-6-cyano-3,4-dihydro-2H-1-benzopyran obtained in the course of Example 5 above and then purified by column chromatography.

$^1$H NMR(CDCl$_3$, 300 MHz) δ1.32(m, 2H), 1.50(s, 3H), 3.80(m, 2H), 4.20(m, 2H), 4.33(s, 1H), 5.85(s, 1H), 6.20(td, 1H), 6.60(d, 1H), 6.78(dd, 1H), 6.95(d, 1H), 7.10(d, 1H), 7.40(td, 1H), 7.50(dd, 1H).

EXAMPLE 14

Synthesis of 2-(2''-(1'',3''-dioxolane))-2-methyl-4-(1'-(2'-oxo-1',2'-dihydropyridyl))-6-nitro-2H-1-benzopyran Similarly to Example 12 above, the title compound was prepared using 2-dimethoxy-methyl-2-methyl-3-hydroxy-4-(1'-(2'-oxo-1',2'-dihydropyridyl))-6-nitro-3,4-dihydro-2H-1-benzopyran obtained in the course of Example 6 above and then purified by column chromatography.

$^1$H NMR(CDCl$_3$, 300 MHz) δ1.50(s, 3H), 3.85(m, 2H), 4.00(m, 2H), 4.38(s, 1H), 5:90(s, 1H), 6.20(td, 1H), 6.70(d, 1H), 6.90(dd, 1H), 7.05(d, 1H), 7.35(dt, 1H), 7.80(d, 1H), 8.05(dd, 1H).

EXAMPLE 15

Synthesis of 2-(2''-(1'',3''-dioxane))-2-methyl-4-(1'-(2'-oxo-1',2'-dihydropyridyl))-6-nitro-2H-1-benzopyran Similarly to Example 13 above, the title compound was prepared using 2-dimethoxy-methyl-2-methyl-3-hydroxy-4-(1'-(2'-oxo-1',2'-dihydropyridyl))-6-nitro-3,4-dihydro-2H-1-benzopyran obtained in step 1 of Example 6 above and then purified by column chromatography.

$^1$H NMR(CDCl$_3$, 300 MHz) δ1.30(m, 2H), 1.52(s, 3H), 3.80(m, 2H), 4.20(m, 2H), 4.35(s, 1H), 5.90(s, 1H), 6.30(td, 1H), 6.70(d, 1H), 6.92(dd, 1H), 7.10(d, 1H), 7.40(dt, 1H), 7.85(d, 1H), 8.10(dd, 1H).

EXAMPLE 16

Synthesis of (+) and (−) 2-dimethoxymethyl-2-methyl-4-(2'-oxo-1'-pyrrolidinyl)-6-cyano-2H-1-benzopyran Step 1) Synthesis of (+) and (−) 2-dimethoxymethyl-2-methyl-3-(O-α-methoxy-α-phenylacetoxy)-4-(2'-oxo-1'-pyrrolidinyl)-6-cyano-3,4-dihydro-2H-1-benzopyran In 50 ml of ethyl acetate was dissolved with heating 1.0 g (2.73 mmole) of the compound obtained in step 1 of Example 1 above. To the resultant solution were added 0.68 g (4.10 mmole) of (−)-α-methoxyphenylacetic acid and then 0.67 g (3.28 mmole) of 1,3-dicyclohexyl carbodiimide at room temperature. Subsequently, 0.040 g (0.33 mmole) of 4-dimethylaminopyridine as a catalyst was added. The resultant mixture was stirred for 24 hours. Dicyclohexyl urea in the form of a white solid produced during the reaction as a side-product was removed by filtration, and the remaining filtrate was concentrated and purified by silica gel column chromatography using a mixture of hexane and ethyl acetate (1:1) as an eluent to obtain 0.70 g (1.36 mmole, yield 50%) of (+) dimethoxymethyl-3-(O-α-methoxy-α-phenylacethoxy)-4-(2'-oxo-1'-pyrrolidinyl)-6-cyano-3,4-dihydro-2H-1-benzopyran having Rf value of 0.23 and 0.54 g (1.05 mmole, yield 38%) of (−) dimethoxymethyl-3-(O-α-methoxy-α-phenylacethoxy)-4-(2'-oxo-1'-pyrrolidinyl)-6-cyano-3,4-dihydro-2H-1-benzopyran having Rf value of 0.30.

Step 2) Synthesis of (+) and (−) dimethoxymethyl-2-methyl-3-hydroxy-4-(2'-oxo-1'-pyrrolidinyl)-6-cyano-3,4-dihydro-2H-1-benzopyran To a solution of 0.70 g (1.36 mmole) of (+) isomer obtained in step 1 dissolved in 10 ml of a mixture of methanol and water (5:1) was slowly added 86 mg (2.04 mmole) of LiOH.H$_2$O at 0° C. The reaction mixture was stirred for 2 hours. From the reaction mixture methanol solvent was removed under reduced pressure. The remaining solution was diluted with 50 ml of ethyl acetate, washed with saturated sodium chloride solution (50 ml×2) and purified by silica gel column chromatography using ethyl acetate as an eluent to obtain 0.43 g (1.17 mmole, yield 86%) of (+) isomer of the title compound as a white solid. Similarly, to a solution of 0.54 g (1.05 mmole) of (−) isomer obtained in step 1 dissolved in 10 ml of a mixture of methanol and water (5:1) was slowly added 66 mg (1.58 mmole) of LiOH.H$_2$O at 0° C. The reaction mixture was stirred for 2 hours. From the reaction mixture methanol solvent was removed under reduced pressure. The remaining solution was diluted with 50 ml of ethyl acetate and washed with saturated sodium chloride solution (50 ml×2). The organic layer was dried over anhydrous magnesium sulfate, concentrated under reduced pressure and purified by silica gel column chromatography using ethyl acetate as an eluent to obtain 0.31 g (0.85 mmole, yield 81%) of (−) isomer of the title compound as a white solid.

Step 3) Synthesis of (+) and (−) 2-dimethoxymethyl-2-methyl-4-(2'-oxo-1'-pyrrolidinyl)-6-cyano-2H-1-benzopyran To a solution of 0.43 g (1.17 mmole) of (+) isomer obtained in step 2 dissolved in 5 ml of dioxane was added 94 mg (2.34 mmole) of NaOH. The resultant solution was heated to reflux for 1 hour and distilled to remove dioxane solvent therefrom. The remaining solution was diluted with 50 ml of ethyl acetate and washed with saturated sodium chloride solution (50 ml×2). The organic layer was dried over anhydrous magnesium sulfate, concentrated under reduced pressure and purified by silica gel column chromatography using a mixture of hexane and ethyl acetate (1:4) as an eluent to obtain 0.35 g (1.01 mmole, yield 85%) of (+) isomer of the title compound having R$_f$ value of 0.4 as a white solid. Similarly, to a solution of 0.31 g (0.85 mmole) of (−) isomer obtained in step 2 dissolved in 5 ml of dioxane was added 68 mg (1.7 mmole) of NaOH. The resultant solution was heated to reflux for 1 hour and distilled to remove dioxane solvent therefrom. The remaining solution was diluted with 50 ml of ethyl acetate and washed with saturated sodium chloride solution (50 ml×2). The organic layer was dried over anhydrous magnesium sulfate, concentrated under reduced pressure and purified by silica gel column chromatography using a mixture of hexane and ethyl acetate (1:4) as an eluent to obtain 0.32 g (0.92 mmole, yield 87%) of (−) isomer of the title compound as a white solid.

$[\alpha]_D^{20} = +80.7$ (c=0.30, CHCl$_3$).
$[\alpha]_D^{20} = -80.9$ (c=0.33, CHCl$_3$).

Activity Test

The activity of the formula (I) compounds of the present invention was tested by employing the tail-cuff method described in references [see, e.g., I. M. Claxton, M. G. Palfreyman, R. H. Poyster and R. L. Whiting, *European Journal of Phalmacology* 37, 179(1976)]. After administration of the test compound of formula (I) to sets of spontaneously hypertensive rats, maximum blood pressure-lowering activity was determined by measuring the lowering effect on systolic blood pressure. The results of the test are shown in Table 1.

Further, the relaxation activity on respiratory smooth muscle was determined as follows: Guinea pig trachea muscle was made to be contracted with histamine; and then the test compound of the present invention was administered thereto; and the concentration of the test compound which was required in relaxing 50% level of the contraction was determined and designated as EC$_{50}$. These EC$_{50}$ values for the test compounds are shown in Table 1.

TABLE 1

| Example No. of Compound Employed | Blood Pressure-Lowering Activity | | Trachea Relaxation Activity, EC$_{50}$ |
|---|---|---|---|
| | Dose (mg/kg) | % | |
| 1 | 0.3 | 24 | $1.5 \times 10^{-4}$ M |
| | 1.0 | 43 | |
| 3 | 0.1 | 6.9 | $1.09 \times 10^{-5}$ M |
| 7 | 1.0 | 41 | $5.0 \times 10^{-5}$ M |
| 9 | 0.1 | 20.6 | $1.71 \times 10^{-5}$ M |
| 11 | 0.1 | 48 | $5 \times 10^{-5}$ M |
| 16(−)* | 0.3 | 28 | $1.4 \times 10^{-4}$ M |
| | 1.0 | 55 | |
| Cromakalim(−)* | 0.3 | 39 | $2.7 \times 10^{-6}$ M |

*represents isomeric form.

As shown by Table 1, the compounds of the present invention have a superior selectivity in the blood pressure-lowering activity over the reference compound, Cromakalim, which is one of the most commercially popular drugs in the market.

Toxicity Test

The toxicity test of the Formula (1) compounds was conducted as follows:

The compounds prepared in Examples 1 and 11 were orally administered to sets of rats, which had a body weight of 100–120 g and were about four week-old. Six pairs (each pair consisting of a male and a female) of the rats were used in the test. The number of the rats which died over a period of 48 hours was reported. The results of the test are shown in Table 2.

TABLE 2

| Example No. of the Compound Employed | Dose (mg/kg) | Lethal Rate (%) | LD$_{50}$* |
|---|---|---|---|
| 1 | 10 | 0 | >50 mg/kg |
| | 20 | 8 | |
| | 50 | 25 | |
| 11 | 10 | 0 | >50 mg/kg |
| | 20 | 35 | |
| | 50 | 35 | |

*LD$_{50}$ (lethal dose) represents the amount of a test compound which causes a 50% lethal rate As shown above, the compounds of the present invention are judged to be safe for use, especially at the amount to be administered.

We claim:
1. A benzopyran derivative of formula (I)

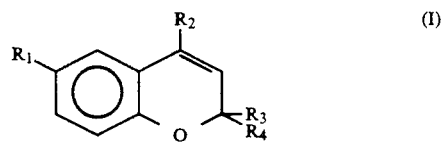

wherein:
R$_1$ is —CN, —NO$_2$, —OCX$_1$X$_2$X$_3$, —NH$_2$, —NHSO$_2$R$^A$,

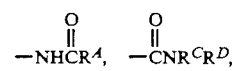

—$SO_2R^C$ or —$SO_2NR^CR^D$ wherein $X_1$, $X_2$ and $X_3$ are, each independently, a fluorine, chlorine or hydrogen atom; $R^A$ and $R^B$ are, each independently, an amino, $C_{1-6}$ alkoxy, $C_{1-6}$ alkyl group or an optionally substituted phenyl group with a halogen atom, or a straight or branched $C_{1-3}$ alkyl group; and $R^C$ and $R^D$ are, each independently, a hydrogen atom or a $C_{1-6}$ alkyl group, or an optionally substituted phenyl group with a halogen atom or a straight or branched $C_{1-3}$ alkyl group;

$R_2$ is

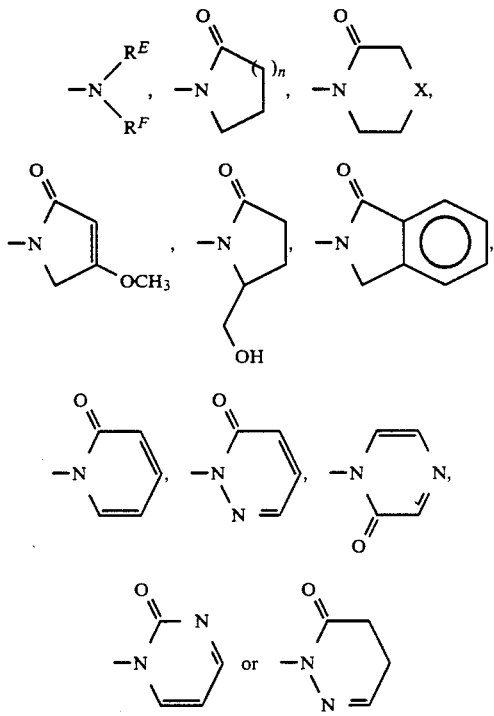

wherein $R^E$ is a hydrogen atom, or a $C_{1-6}$ alkyl, cyclopropyl, cyclopropylmethyl or benzyl group; $R^F$ is —$COR^A$ or —$CSR^A$; X is O, S or $NR^C$; and, n is an integer from 0 to 3, wherein $R^A$ and $R^C$ are the same as defined above;

$R_3$ is a $C_{1-4}$ straight or branched alkyl group; and $R_4$ is

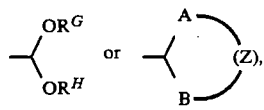

wherein $R^G$ and $R^H$ are, each independently, a $C_{1-6}$ alkyl group or phenyl group; A and B are, each independently, S or O; and Z is a $C_{1-3}$ straight or branched alkyl group.

2. The benzopyran derivative of claim 1 wherein $R_1$ is —CN, —$NO_2$, —$OCF_3$ or —$SO_2NR^CR^D$ wherein $R^C$ and $R^D$ are, each independently, a $C_{1-6}$ alkyl group;

$R_2$ is

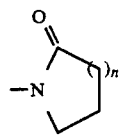

wherein n is an integer from 0 to 2,

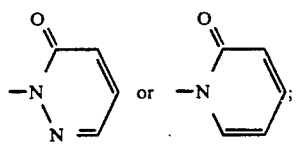

and
$R_4$ is

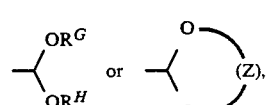

wherein $R^G$ and $R^H$ are, each independently, a $C_{1-3}$ alkyl group and Z is the same as defined in claim 1.

3. The benzopyran derivative of claim 1 wherein $R_1$ is —CN, —$NO_2$ or —$OCF_3$, $R_2$ is

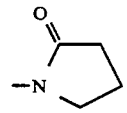

and $R_4$ is

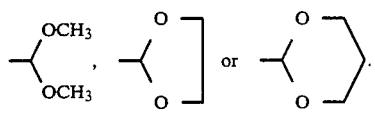

4. The benzopyran derivative of claim 1 which is selected from the group consisting of:
2-dimethoxymethyl-2-methyl-4-(2'-oxo-1'-pyrrolidinyl)-6-nitro-2H-1-benzopyran;
2-dimethoxymethyl-2-methyl-4-(2'-oxo-1'-pyrrolidinyl)-6-cyano-2H-1-benzopyran;
2-dimethoxymethyl-2-methyl-4-(2'-oxo-1'-pyrrolidinyl)-6-trifluoromethoxy-2H-1-benzopyran;
2-(2"-(1",3"-dioxolane))-2-methyl-4-(2'-oxo-1'-pyrrolidinyl)-6-nitro-2H-1-benzopyran;
2-(2"-(1",3"-dioxolane))-2-methyl-4-(2'-oxo-1'-pyrrolidinyl)-6-cyano-2H-1-benzopyran; and
2-(2"-(1",3"-dioxolane))-2-methyl-4-(2'-oxo-1'-pyrrolidinyl)-6-trifluoromethoxy-2H-1-benzopyran.

5. A pharmaceutical composition comprising the compound of formula (I) as defined in claim 1 as an active ingredient.

* * * * *